(12) United States Patent
Alland et al.

(10) Patent No.: US 6,821,769 B2
(45) Date of Patent: Nov. 23, 2004

(54) INIB, INIA AND INIC GENES OF MYCOBACTERIA AND METHODS OF USE

(75) Inventors: David Alland, Dobbs Ferry, NY (US); Barry R. Bloom, Hastings-on-Hudson, NY (US); William R. Jacobs, Jr., City Island, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 185 days.

(21) Appl. No.: 09/918,951

(22) Filed: Jul. 31, 2001

(65) Prior Publication Data

US 2002/0151008 A1 Oct. 17, 2002

Related U.S. Application Data

(63) Continuation of application No. 09/177,349, filed on Oct. 23, 1998, now Pat. No. 6,268,201.

(51) Int. Cl.$^7$ .......................... C12N 1/12; A61K 39/04; A61K 39/40; C07H 21/02; C07H 21/04
(52) U.S. Cl. ................. 435/253.1; 424/168.1; 424/248.1; 435/320.1; 435/863; 435/864; 435/865; 435/866; 536/23.1; 536/23.7; 536/24.32
(58) Field of Search .......................... 424/168.1, 248.1; 435/253.1, 320, 863, 864, 865, 866; 536/23.1, 23.7, 24.32

(56) References Cited

PUBLICATIONS

Altschul et al., Gapped BLAST and PSI–BLAST: a new generation of protein database search programs. Nucleic Acids REs., 25:3389–3402, 1997.
Bairoch et al., The Prosite database, its status in 1997. Nucleic Acids Res., 25:217–221, 1997.
Banerjee et al., inhA, a gene encoding a target for isoniazid and ethionamide in *Mycobacterium tubreculosis*. Science, 263:227–230, 1994.
Cole et al., Deciphering the biology of *Mycobacterium tuberculosis* from the complete genome sequence, Nature, 393:537–544, 1998.
de Saizieu et al., Bacterial transcript imaging by hybridization of total RNA to olignucleotide arrays. Nature Biotech., 16:45–48, 1998.
Garbe et al., Isoniazid induced expression of the antigen 85 complex in Mycobacterium tuberculosis. Antimicrobial Agents and Chemotherapy, 40:1754–1756, 1996.
Kinger and Tyagi, Identification and Cloning of genes differentially expressed in the virulent strain of *Mycobacterium tuberculosis*. Gene, 131:113–117, 1993.
Mathiopoulos and Sonenshein, Identification of Bacillus subtilis expressed early during sporulation. Mol. Microbiol., 3:1071–1081, 1989.
Mdluli et al., Inhibition of a *Mycobacterium tuberculosis* beta–ketoacyl ACP synthase by isoniazid. Science, 280:1607–1610, 1998.
Plum and Clark–Cutiss, Induction of *Mycobacterium avium* gene expression following phagocytosis by human macrophages. Infect. and Immun. 62:476–483, 1994.
Wong and McClelland, Stress–inducible gene of salmonella typhimurium identified by arbitrarily primed PCR of RNA. Proc. Natl. Acad. Sci. USA, 91:639–643, 1994.

*Primary Examiner*—Rodney P Swartz
(74) *Attorney, Agent, or Firm*—Amster, Rothstein & Ebenstein LLP

(57) ABSTRACT

This invention relates to the identification, cloning, sequencing and characterization of the iniB, iniA and iniC genes of mycobacteria which are induced by a broad class of antibiotics that act by inhibiting cell wall biosynthesis, including the first line antituberculosis agents, isoniazid and ethambutol. The present invention provides purified and isolated iniB, iniA, iniC and iniB promoter nucleic acids which may comprise the iniBAC operon, as well as mutated forms of these nucleic acids. The present invention also provides one or more single-stranded nucleic acid probes which specifically hybridize to the iniB, iniA, iniC and iniB promoter nucleic acids, and mixtures thereof, which may be formulated in kits, and used in the diagnosis of drug-resistant mycobacterial strain. The present invention also provides methods for the screening and identification of drugs effective against *Mycobacterium tuberculosis* using induction of the iniB promoter.

5 Claims, 9 Drawing Sheets

Cosmid MTCY279:

9048 cac ggctacgaca
9061 tccacggata agttccggac cggcgtaggg gtgccccatt

Cosmid MTY13E10:

```
   1 tcccctaatc ccctaacgcg gcggccaggc cgatcccgat aggtgtttgg ccggcttgcg
  61 gatcagaccc cgatttcggg gtgaggcgga atccatagcg tcgatggcac agcgccggtc
 121 acgccggcga acagcttctt cgattgaagg gaaatgaaga tgacctcgct tatcgattac
 181 atcctgagcc tgttccgcag cgaagacgcc gcccggtcgt tcgttgccgc tccgggacgg
 241 gccatgacca gtgccgggct gatcgatatc gcgccgcacc aaatctcatc ggtggcggcc
 301 aatgtggtgc cgggtctgaa tctgggtgcc ggcgacccca tgagcggatt gcggcaggcc
 361 gtcgccgctc ggcatggctt tgcgcaggac gtcgccaatg tcggcttcgc cggtgacgcg
 421 ggcgcggggg tggcaagcgt catcacgacc gatgtcggtg cgggcctggc tagcggactg
 481 ggtgctgggt tcctgggtca gggtggcctg gctctcgccg cgtcaagcgg tggtttcggc
 541 ggtcaggtcg gcttggctgc ccaggtcggt ctgggtttta ctgccgtgat tgaggccgag
 601 gtcggcgctc aggttggtgc tgggttaggt attgggacgg gtctgggtgc tcaggccggt
 661 atgggctttg gcggcggggt tggcctgggt ctgggtggtc aggccggcgg tgtgatcggt
 721 gggagcgcgg ccggggctat cggtgccggc gtcggcggtc gcctaggcgg caatggccag
 781 atcggagttg ccggccaggg tgccgttggc gctggtgtcg gcgctggtgt cggcggccag
 841 gcgggcatcg ctagccagat cggtgtctca gccggtggtg ggctcggcgg cgtcggcaat
 901 gtcagcggcc tgaccggggt cagcagcaac gcagtgttgg cttccaacgc aagcggccag
 961 gcggggttga tcgccagtga aggcgctgcc ttgaacggcg ctgctatgcc tcatctgtcg
1021 ggcccgttag ccggtgtcgg tgtgggtggt caggccggcg ccgctggcgg cgccgggttg
1081 ggcttcggag cggtcgggca cccgactcct cagccggcgg ccctgggcgc ggctggcgtg
1141 gtggccaaga ccgaggcggc tgctggagtg gttggcgggg tcggcggggc aaccgcggcc
1201 ggggtcggcg gggcacacgg cgacatcctg gccacgagg agccgcact gggcagtgtc
1261 gacacggtca acgccggtgt cacgcccgtc gagcatggct tggtcctgcc cagtggcccc
1321 ctgatccacg gcggtaccgg cggctatggc ggcatgaacc cgccagtgac cgatgcgccg
1381 gcaccgcaag ttccggcgcg ggcccagccg atgaccacgg cggccgagca cacgccggcg
1441 gttacccaac cgcagcacac gccggtcgag ccgccggtcc acgataagcc gccgagccat
1501 tcggtgtttg acgtcggtca cgagccgccg gtgacgcaca cgccgccggc gcccatcgaa
1561 ctgccgtcgt acggcctttt cggactaccc gggttctgat tcgcgagccg atttcacgaa
1621 ccggtgggga cgttcatggt ccccgccggt ttgtgcgcat accgtgatct gaggcgtaaa
1681 cgagcgagaa agtggggcga cacggtgacc cagcccgatg acccacgtcg ggtcggtgtg
1741 atcgtcgaac tgatcgatca cactatcgcc atcgccaaac tgaacgagcg tggtgatcta
1801 gtacagcggt tgacgcgggc tcgccagcgg atcaccgacc cgcaggtccg tgtggtgatc
```

FIG. 5A

```
1861 gccgggctgc tcaaacaggg caagagtcaa ttgctcaatt cgttgctcaa cctgcccgcg
1921 gcgcgagtag gcgatgacga ggccaccgtg gtgatcaccg tcgtaagcta cagcgcccaa
1981 ccgtcggccc ggcttgtgct ggccgccggg cccgacggga caaccgcagc ggttgacatt
2041 cccgtcgatg acatcagcac cgatgtgcgt cgggctccgc acgccggtgg ccgcgaggtg
2101 ttgcgggtcg aggtcggcgc gcccagcccg ctgctgcggg gcgggctggc gtttatcgat
2161 actccgggtg tgggcggcct cggacagccc cacctgtcgg cgacgctggg gctgctaccc
2221 gaggccgatg ccgtcttggt ggtcagcgac accagccagg aattcaccga acccgagatg
2281 tggttcgtgc ggcaggccca ccagatctgt ccggtcgggg cggtcgtggc caccaagacc
2341 gacctgtatc cgcgctggcg ggagatcgtc aatgccaatg cagcacatct gcagcgggcc
2401 cgggttccga tgccgatcat cgcagtctca tcactgttgc gcagccacgc ggtcacgctt
2461 aacgacaaag agctcaacga agagtccaac tttccggcga tcgtcaagtt tctcagcgag
2521 caggtgcttt cccgcgcgac ggagcgagtg cgtgctgggg tactcggcga aatacgttcg
2581 gcaacagagc aattggcggt gtctctaggt tccgaactat cggtggtcaa cgacccgaac
2641 ctccgtgacc gacttgcttc ggatttggag cggcgcaaac gggaagccca gcaggcggtg
2701 caacagacag cgctgtggca gcaggtgctg ggcgacgggt tcaacgacct gactgctgac
2761 gtggaccacg acctacgaac ccgcttccgc accgtcaccg aagacgccga gcgccagatc
2821 gactcctgtg acccgactgc gcattgggcc gagattggca acgacgtcga gaatgcgatc
2881 gccacagcgg tcggcgacaa cttcgtgtgg gcataccagc gttccgaagc gttggccgac
2941 gacgtcgctc gctcctttgc cgacgcgggg ttggactcgg tcctgtcagc agagctgagc
3001 ccccacgtca tgggcaccga cttcggccgg ctcaaagcgc tgggccggat ggaatcgaaa
3061 ccgctgcgcc ggggccataa aatgattatc ggcatgcggg gttcctatgg cggcgtggtc
3121 atgattggca tgctgtcgtc ggtggtcgga cttgggttgt tcaacccgct atcggtgggg
3181 gccgggttga tcctcggccg gatggcatat aaagaggaca aacaaaaccg gttgctgcgg
3241 gtgcgcagcg aggccaaggc caatgtgcgg cgcttcgtcg acgacatttc gttcgtcgtc
3301 agcaaacaat cacgggatcg gctcaagatg atccagcgtc tgctgcgcga ccactaccgc
3361 gagatcgccg aagagatcac ccggtcgctc accgagtccc tgcaggcgac catcgcggcg
3421 gcgcaggtgg cggaaaccga gcgggacaat cgaattcggg aacttcagcg gcaattgggt
3481 atcctgagcc aggtcaacga caaccttgcc ggcttggagc caaccttgac gccccgggcg
3541 agcttgggac gagcgtgagc accagcgacc gggtccgcgc gattctgcac gcaaccatcc
3601 aggcctaccg gggtgcgccg gcctatcgtc agcgtggcga cgttttttgc cagctggacc
3661 gcatcggtgc gcgcctagcc gaaccgctgc gcatcgcgtt ggctggcaca ctcaaggccg
3721 gaaaatccac tctcgtcaac gcccttgtcg gcgacgacat cgctccgacc gatgccaccg
3781 aggccacccg gattgtgacc tggttccggc acggtccgac accgcgggtc accgccaacc
3841 atcgcggcgg tcgacgcgcc aacgtgccga tcacccgtcg ggcgggctg agtttcgacc
3901 tgcgcaggat caacccggcc gagctgatcg acctggaagt cgagtggcca gccgaggaac
3961 tcatcgacgc caccattgtt gacaccccgg gaacgtcgtc gttggcatgc gatgcctccg
4021 agcgcacgtt gcggctgctg gtcccgccg acggggtgcc tcgggtggat gcggtggtgt
4081 tcctgttgcg cacccctgaac gccgctgacg tcgcgctgct caaacagatc ggtgggctgg
4141 tcggcgggtc ggtgggagcc ctgggcatca tcggggtggc gtctcgcgcg gatgagatcg
4201 gcgcgggccg catcgacgcg atgctctcgg ccaacgacgt ggccaagcgg ttcacccgcg
4261 aactgaacca gatgggcatt tgccaggcgg tggtgccggt atccggactt cttgcgctga
```

FIG. 5B

```
4321 ccgcgcgcac actgcgccag accgagttca tcgcgctgcg caagctggcc ggtgccgagc
4381 gcaccgagct caatagggcc ctgctgagcg tggaccgttt tgtgcgccgg gacagtccgc
4441 taccggtgga cgcgggcatc cgtgcgcaat tgctcgagcg gttcggcatg ttcggcatcc
4501 ggatgtcgat tgccgtgctg gcggccggcg tgaccgattc gaccgggctg gccgccgaac
4561 tgctggagcg cagcgggctg gtggcgctgc gcaatgtgat agaccagcag ttcgcgcagc
4621 gctccgacat gcttaaggcg cataccgcct tggtctcctt gcgccgattc gtgcagacgc
4681 atccggtgcc ggcgaccccg tacgtcattg ccgacatcga cccgttgcta gccgacaccc
4741 acgccttcga agaactccga atgctaagcc ttttgccttc gcgggcaacg acattgaacg
4801 acgacgaaat cgcgtcgctg cgccgcatca tcggcgggtc gggcaccagt gccgccgctc
4861 ggctgggcct ggatcccgcg aattctcgcg aggccccgcg cgccgcgctg gccgcagcgc
4921 aacactggcg tcgccgtgcg gcgcatccac tcaacgatcc gttcactacc agggcctgtc
4981 gcgcggcggt gcgcagcgcc gaggcgatgg tggcggagtt ctctgctcgc cgctga
```

FIG. 5C

Rv0341 (iniB)

MTSLIDYILSLFRSEDAARSFVAAPGRAMTSAGLIDIAPHQISSVAANVVPGLNLGAGDPMSGL
RQAVAARHGFAQDVANVGFAGDAGAGVASVITTDVGAGLASGLGAGFLGQGGLALAASSGG
FGGQVGLAAQVGLGFTAVIEAEVGAQVGAGLGIGTGLGAQAGMGFGGGVGLGLGGQAGGVI
GGSAAGAIGAGVGGRLGGNGQIGVAGQGAVGAGVGAGVGGQAGIASQIGVSAGGGLGGVGN
VSGLTGVSSNAVLASNASGQAGLIASEGAALNGAAMPHLSGPLAGVGVGGQAGAAGGAGLG
FGAVGHPTPQPAALGAAGVVAKTEAAAGVVGGVVGGATAAGVVGGAHGDILGHEGAALGSVDT
VNAGVTPVEHGLVLPSGPLIHGGTGGYGGMNPPVTDAPAPQVPARAQPMTTAAEHTPAVTQ
PQHTPVEPPVHDKPPSHSVFDVGHEPPVTHTPPAPIELPSYGLFGLPGF

Rv0342 (iniA)

MVPAGLCAYRDLRRKRARKWGDTVTQPDDPRRVGVIVELIDHTIAIAKLNERGDLVQRLTRA
RQRITDPQVRVVIAGLLKQGKSQLLNSLLNLPAARVGDDEATVVITVVSYSAQPSARLVLAAGP
DGTTAAVDIPVDDISTDVRRAPHAGGREVLRVEVGAPSPLLRGGLAFIDTPGVGGLGQPHLSA
TLGLLPEADAVLVVSDTSQEFTEPEMWFVRQAHQICPVGAVVATKTDLYPRWREIVNANAAH
LQRARVFMPIIAVSSLLRSHAVTLNDKELNEESNFPAIVKFLSEQVLSRATERVRAGVLGEIRSA
TEQLAVSLGSELSVVNDPNLRDRLASDLERRKREAQQAVQQTALWQQVLGDGFNDLTADVD
HDLRTRFRTVTEDAERQIDSCDPTAHWAEIGNDVENAIATAVGDNFVWAYQRSEALADDVA
RSFADAGLDSVLSAELSPHVMGTDFGRLKALGRMESKPLRRGHKMIIGMRGSYGGVVMIGML
SSVVGLGLFNPLSVGAGLILGRMAYKEDKQNRLLRVRSEAKANVRRFVDDISFVVSKQSRDRL
KMIQRLLRDHYREIAEEITRSLTESLQATIAAAQVAETERDNRIRELQRQLGILSQVNDNLAGL
EPTLTPRASLGRA

Rv0343 (iniC)

MSTSDRVRAILHATIQAYRGAPAYRQRGDVFCQLDRIGARLAEPLRIALAGTLKAGKSTLVNAL
VGDDIAPTDATEATRIVTWFRHGPTPRVTANHRGGRRANVPITRRGGLSFDLRRINPAELIDL
EVEWPAEELIDATIVDTPGTSSLACDASERTLRLLVPADGVPRVDAVVFLLRTLNAADVALLKQI
GGLVGGSVGALGIIGVASRADEIGAGRIDAMLSANDVAKRFTRELNQMGICQAVVPVSGLLAL
TARTLRQTEFIALRKLAGAERTELNRALLSVDRFVRRDSPLPVDAGIRAQLLERFGMFGIRMSI
AVLAAGVTDSTGLAAELLERSGLVALRNVIDQQFAQRSDMLKAHTALVSLRRFVQTHPVPATP
YVIADIDPLLADTHAFEELRMLSLLPSRATTLNDDEIASLRRIIGGSGTSAAARLGLDPANSREA
PRAALAAAQHWRRRAAHPLNDPFTTRACRAAVRSAEAMVAEFSARR

FIG. 6

INIB, INIA AND INIC GENES OF MYCOBACTERIA AND METHODS OF USE

CO-PENDING APPLICATION

This application is a Continuation of U.S. application Ser. No. 09/177,349 filed on Oct. 23, 1998, now U.S. Pat. No. 6,268,201 issued on Jul. 31, 2001.

BACKGROUND OF THE INVENTION

This invention is based upon the discovery by the inventors of the iniB, inia and iniC genes, and the proteins encoded by these genes which are induced by a broad class of antibiotics that act by inhibiting cell wall biosynthesis, including the first line antituberculosis agents, isoniazid (INH) and ethambutol (EMB). The discovery of the iniB, inia and iniC genes, and the proteins encoded by these genes will have important implications in the identification of drugs effective against *M. tuberculosis*, as well as the treatment of drug-resistant mycobacterial strains.

Many highly effective classes of antibiotics work by inhibiting microbial cell wall biosynthesis. In *M. tuberculosis* several antibiotics, including isoniazid and ethambutol, appear to act by this general mechanism.

EMB is a selective antimycobacterial drug recommended for clinical use in 1996 (Karlson, A. G., Am Rev Resp Dis 84, 905–906 (1961)). Today, EMB remains an important component of tuberculosis treatment programs. Unfortunately, resistance to ethambutol has been described in 2–4% of clinical isolates of *M. tuberculosis* in the USA and other countries, and is prevalent among isolates from patients with multidrug-resistant tuberculosis (Bloch, AB., Cauthen, GM., Onorato, IM., et al. Nationwide survey of drug-resistant tuberculosis in the United States. *JAMA* 271, 665–671 (1994)).

EMB targets the mycobacterial cell wall, a unique structure among prokaryotes which consists of an outer layer of mycolic acids covalently bound to peptidoglycan via the arabinogalactan (Besra, G. S. & Chatterjee, D. in *Tuberculosis. Pathogenesis, protection, and control* (ed Bloom, B. R.) 285–306 (ASM Press, Washington D.C., 1994)). Lipoarabinomannan, another cell wall component of significant biological importance, shares with arabinogalactan the overall structure of the arabinan polymer (Chatterjee, D., et al., *J. Biol Chem* 266, 9652–9660 (1991)).

EMB inhibits the in vivo conversion of [$^{14}$C]glucose into cell wall arabinan (Takayama, K. & Kolburn, J. O., *Antimicrob Agents Chemother* 33, 143–1499 (1989)), and results in the accumulation of the lipid carrier decaprenyl-P-arabinose (Wolucka, B. A., et al., *J Biol Chem* 269, 23328–23335 (1994)), which suggest that the drug interferes with the transfer of arabinose to the cell wall acceptor. The synthesis of lipoarabinomannan is also inhibited in the presence of EMB (Deng, L., et al. *Antimicrob Agents Chemother* 39, 694–701 (1995)), (Mikusova, K., et al., Antimicrob Agents Chemother 39, 2484–2489 (1995)); again, this indicates a specific effect on arabinan biosynthesis.

Isoniazid (INH) is a front-line drug in the treatment of tuberculosis. INH is a prodrug that requires activation by the catalase-peroxidase enzyme (katG) to an active form (Zhang et al., (1992) Nature 358, 591–593). It is likely that INH acts by blocking mycolic acid biosynthesis as evidenced by the physical and biochemical changes that occur at the same time as INH toxicity (Winder and Collins, (1970) J. Gen. Microbiol. 63, 41; Davidson and Takayama, (1979) Antibicrob. Agents Chemother. 16, 104). Treatment with INH leads to the accumulation of saturated hexacosanoic acid, and has been shown to inhibit the action of several enzymes thought to be involved in mycolic acid biosynthesis including InhA (Banedjee et al., (1994) Science 263, 227–230) and kasA (Mdluli et al., (1998) Science 280, 1607–1610).

Recent reports have documented a significant increase in the global incidence of drug resistant tuberculosis. Thus, there is a need for the identification and characterization of new target genes and proteins to aid in screening for new drugs. This would require the identification of genes that participate in the biosynthesis of the mycobacterial cell wall and the identification of mutants of these genes encoding proteins that confer resistance to drugs. While it is possible that the iniB, iniA, and iniC gene products are not in themselves targets for currently available antibiotics, these proteins may act to protect *M. tuberculosis* and other mycobacteria from toxic effects that occur when cell wall biosynthesis is inhibited by antibiotics. Novel drugs that inhibit the iniB, iniA, and iniC proteins may therefore act synergistically with other cell wall active antibiotics and prove useful in treating tuberculosis, including drug resistant tuberculosis.

Current high throughput drug screens do not usually assay agents at high concentrations because nonspecific toxic effects are common. This strategy may miss important compounds that could be modified to have higher potency. This is a particular concern for screening compounds against *M. tuberculosis* because many drugs may have difficulty penetrating through its lipid laden cell wall. Thus, there is a great need for new drug screens which overcome the deficiencies of the present screens for compounds against *M. tuberculosis*.

SUMMARY OF THE INVENTION

The present invention is directed to the nucleic acid sequences of the iniB, iniA and iniC genes, and the proteins encoded by these genes which are induced by a broad class of antibiotics that act by inhibiting cell wall biosynthesis, including the first line antituberculosis agents, ethambutol (EMB) and isoniazid. The present invention further provides for the identification, isolation and characterization of these nucleic acid sequences and the proteins which they encode.

The present invention specifically provides purified and isolated nucleic acid sequences of the iniB, iniA, and iniC genes, as well as mutated forms of these genes. The present invention also provides one or more single-stranded nucleic acid probes which specifically hybridize to the nucleic acid sequences of the iniB, iniA, and iniC genes, as well as mutated forms of these genes, and mixtures thereof, which may be formulated in kits, and used in the detection of drug resistant mycobacterial strains.

The present invention also provides purified active iniB, iniA, and iniC proteins encoded by the iniB, iniA, and iniC genes. Also provided are antibodies immunoreactive with the protein(s) expressed by the iniB, iniA, and iniC genes, and analogues thereof, as well as antibodies immunoreactive with the protein(s) expressed by the these genes.

Further provided by the present invention is a method of screening drugs or compounds to determine whether the drug or compound is effective against *Mycobacterium tuberculosis*.

Additional objects of the invention will be apparent from the description which follows.

BRIEF DESCRIPTION OF THE FIGURES

FIG. 1 shows induction of the iniA gene after treatment with different antibiotics. Autoradiographs of a Northern blot containing RNA from *M. tuberculosis* cultures treated either with no antibiotics; isoniazid 0.01 μg/ml; isoniazid 0.1 μg/ml; isoniazid 1 μg/ml; ethambutol 5 μg/ml; streptomycin 5 μg/ml; and rifampin 5 μg/ml. The blots were hybridized first with an iniA DNA probe (top) to examine iniA induction; the blot was then stripped and re-hybridized with a 16S probe (bottom) to confirm equal RNA loading.

FIGS. 2A and 2B show reverse transcription PCR of differentially expressed genes. FIG. 2A: RNA was extracted from log phase *M. tuberculosis* strain Erdman either without (lanes 1–3) or with (4–6) isoniazid added to the bacterial cultures for the last 18 hours. RNA from both cultures was equalized by comparison of the 16S band intensity. RT PCR using three ten-fold dilutions of each RNA and either iniA, asd or 16S specific primers was performed. Induction of iniA and suppression of asd by isoniazid is demonstrated. The amount of 16S RT PCR product is similar for equivalent dilutions, indicating equal amounts of starting RNA. Lanes 7–8 are minus RT controls; and lane 9 a negative PCR control. FIG. 2B: Lack of iniA induction in an isoniazid resistant strain. Cultures of isogenic BCG strain ATCC35735 which is susceptible to isoniazid (lanes 1–6), or ATCC35747 which is resistant to isoniazid (lanes 7–12), were incubated either in the presence or absence of isoniazid for the last 18 hours. Three ten-fold dilutions of RNA extracted from each culture were tested by RT PCR for iniA induction. Induction is seen only in the INH susceptible strain. Lanes 13–16 are minus RT controls; and lane 17 a negative PCR control containing no added template.

FIG. 3 shows the results of the experiments directed to the induction of the iniB promoter.

FIG. 4 shows the results of the experiments directed to the induction of iniB by amino acids.

FIGS. 5A–5C: FIGS. 5A–5C set forth the nucleic acid sequences of the iniB, iniA and iniC genes, and the promoter region of the iniB gene. MTCY279, genebank accession Z97991. Nucleotides 9048–9101 SEQ ID NO:1), then nucleotides 1–159 of *M. tuberculosis* cosmid MTY13E10 (nucleotides 1–159 of SEQ ID NO:2), genebank accession Z95324. For a total of 213 nucleotides. Nucleotide sequences of genes, numbering from MTY13E10 iniB 160–1559 (nucleotides 160–1559 of SEQ ID NO:2); iniA 1636–3558 (nucleotides 1636–3558 of SEQ ID NO:2) and iniC 3555–5036 (nucleotides 3555–5036 of SEQ ID NO:2).

FIG. 6: FIG. 6 sets forth the amino acid sequences encoded by the iniB (SEQ ID NO:3), iniA (SEQ ID NO:4), and iniC (SEQ ID NO:5) genes.

DETAILED DESCRIPTION OF THE INVENTION

Figure 1:
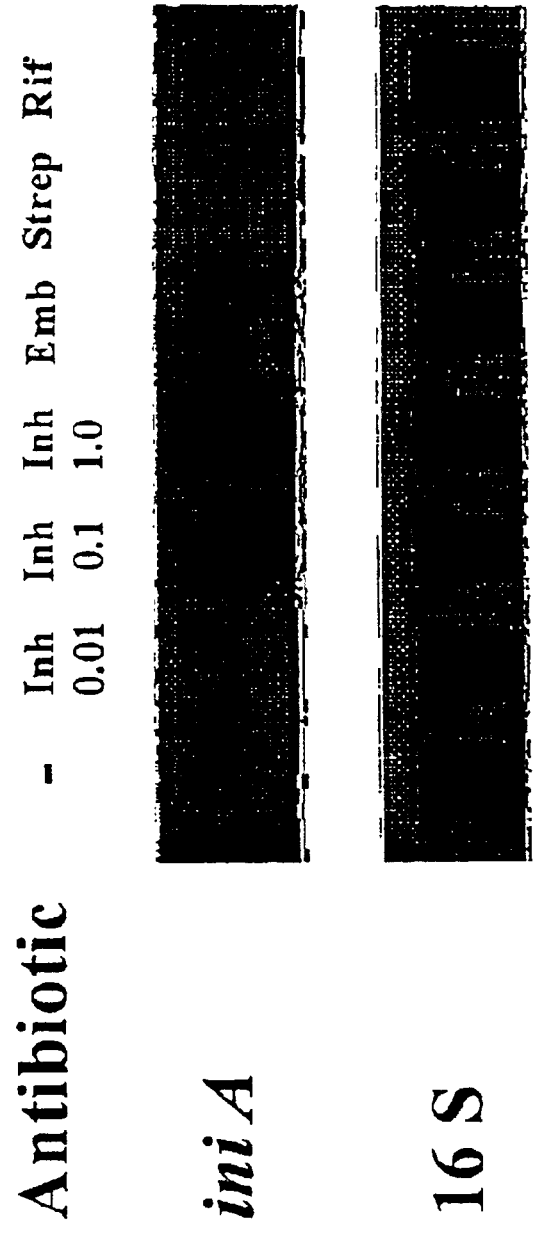
FIG. 1.

The present invention is directed to the nucleic acid sequences of the iniB, iniA and iniC genes, and the proteins encoded by these genes which are induced by a broad class of antibiotics that act by inhibiting cell wall biosynthesis, including the first line antituberculosis agents, ethambutol (EMB) and isoniazid.

The present invention specifically provides purified and isolated nucleic acid sequences of the iniB, iniA, iniC and iniB promoter genes. Also provided are mutated forms of these nucleic acids. It is possible, that the iniB, iniA and iniC genes may form an operon, herein designated the "iniBAC operon" or the "iniA operon". As used herein, an "operon" is a cluster of related genes and their promoters that encode for open reading frames. The "iniBAC operon" as used herein consists of the iniB, iniA and iniC genes arranged in a single operon, as well as the sequences encoding the promoters for the iniBAC genes. The "wild type iniBAC operon" is herein defined as the normal form of the iniB, iniA, and iniC genes which express gene products, and includes degenerate forms. The "mutated iniBAC operon" is the mutated form of the normal iniBAC operon, which contains one or more deletions, insertions, point, substitution, nonsense, missense, polymorphism, or rearrangement mutations, or a combination thereof. As used herein, "nucleic acid" may be genomic DNA, cDNA or RNA, and may be the entire nucleic acid sequence comprising the iniB, iniA, and iniC genes, the nucleic acid sequence of the iniB gene and its promoter, the nucleic acid sequence of the iniB promoter, or any portion of the sequence thereof.

The present invention specifically provides for the iniB, iniA, and iniC nucleic acid sequences isolated from *M. tuberculosis*. These sequences are set forth in FIG. 6. The present invention also provides for the iniB, iniA, and iniC nucleic acid sequences which encodes the amino acid sequence set forth in FIG. 7. The present invention provides for the nucleic acid sequence comprising the iniB promoter region set forth in FIG. 6. FIG. 6 indicates the position of the iniB promoter, however, it is to be understood that the iniB promoter may consist of additional nucleotides upstream from the iniB promoter region indicated in FIG. 6.

The present invention further provides for mutated nucleic acid sequences of the iniB, iniA, and iniC nucleic acid sequences. These mutation(s) may be deletions, insertions, substitutions, missense, nonsense, point or rearrangement mutations, or a combination thereof.

The nucleic acid sequences of the iniB, iniA, and iniC genes can be prepared several ways. For example, they can be prepared by isolating the nucleic acid sequences from a natural source, or by synthesis using recombinant DNA techniques. In addition, mutated nucleic acid sequences of the iniB, iniA, and iniC genes can be prepared using site mutagenesis techniques. The amino acid sequences may also be synthesized by methods commonly known to one skilled in the art (*Modern Techniques of Peptide and Amino Acid Analysis*, John Wiley & Sons (1981); M. Bodansky, *Principles of Peptide Synthesis*, Springer Verlag (1984)). Examples of methods that may be employed in the synthesis of the amino acids sequences, and mutants of these sequences include, but are not limited to, solid phase peptide synthesis, solution method peptide synthesis, and synthesis using any of the commercially available peptide synthesizers. The amino acid sequences, and mutants thereof, may contain coupling agents and protecting groups used in the synthesis of the protein sequences, and are well known to one of skill in the art.

The present invention also provides single-stranded nucleic acid probes and mixtures thereof for use in detecting drug resistance caused by a mutated nucleic acid of the iniB, iniA, or iniC genes. The nucleic acid probes may be DNA, cDNA, or RNA, and may be prepared from the mutated and/or wild type nucleic acid sequences comprising the iniB, iniA, or iniC genes. The probes may be the full length sequence of the nucleic acid sequences comprising the iniB, iniA, or iniC genes, or fragments thereof. Typical probes are 12 to 40 nucleotides in length. The probes may be synthesized using an oligonucleotide synthesizer, and may be labeled with a detectable marker such as a fluorescence, enzyme or radiolabeled markers including $^{32}P$ and biotin, and the like. Combinations of two or more labeled probes corresponding to different regions of the iniB, iniA, or iniC genes also may be included in kits to allow for the detection and/or analysis of the iniB, iniA, and iniC genes by hybridization.

Specifically, the nucleic acid sequences of the iniB, iniA, or iniC genes may be used to produce probes which can be used in the identification, treatment and prevention of diseases caused by microorganisms and to determine whether various drugs are effective against mycobacterial strains.

The present invention also provides purified active iniB, iniA, and iniC proteins, encoded by the iniB, iniA, and iniC genes. The proteins may be expressed by the wild type or mutated nucleic acid sequences of the iniB, iniA, and iniC genes, or an analogue thereof. As used herein, "analogue" means functional variants of the wild type protein, and includes iniB, iniA, and iniC proteins isolated from bacterial sources other then mycobacteria, as well as functional variants thereof. The proteins may also be isolated from native cells, or recombinantly produced.

The present invention also provides antibodies immunoreactive with the proteins expressed by the iniB, iniA, and iniC genes, and analogues thereof, as well as antibodies immunoreactive with the proteins expressed by the mutated nucleic acid sequences of the iniB, iniA, and iniC genes. The antibodies may be polyclonal or monoclonal and are produced by standard techniques. The antibodies may be labeled with standard detectable markers (e.g. chemiluminescent detection systems and radioactive labels such as $^{125}$I) for detecting the wild type and mutated iniB, iniA, and iniC genes. The antibodies may also be presented in kits with detectable labels and other reagents and buffers for such detection.

The present invention also provides for a method of assessing the susceptibility of a mycobacterium to EMB and/or isoniazid in a clinical sample comprising isolating the mycobacterial chromosomal DNA from a clinical sample, preparing oligonucleotides utilizing the wild-type or mutant iniB, iniA, or iniC nucleic acid sequences, amplifying the region of the iniB, iniA, or iniC gene from the clinical sample, and determining whether a mutated iniB, iniA, or iniC gene exists in the mycobacterial strain in the clinical sample.

The mycobacteria that may be assessed by this method of the present invention include, but are not limited to, *Mycobacterium tuberculosis, Mycobacterium avium, Mycobacterium smegmatis, Mycobacterium bovis BCG, Mycobacterium leprae, Mycobacterium africanum,* and *Mycobacterium intracellulare.*

Non-limiting examples of clinical samples that may assessed by the methods of the present invention are urine, feces, blood, serum, mucus, cerebrospinal fluid, and any mixture thereof.

The present invention also provides for a method of treating a mycobacterial infection in a subject by obtaining anti-DNA or anti-RNA nucleic acid sequences capable of inhibiting the mRNA activity of the iniB, iniA, or iniC genes of a mycobacterium, utilizing a wild type or the mutant nucleic acid of the iniB, iniA, or iniC genes, and administering an amount of said nucleic acid sequences, either alone or in combination with other compositions to treat the mycobacterial infection in a subject.

The anti-DNA or anti-RNA nucleic acid sequences employed in the method may be mutant or wild-type nucleic acid sequences of the iniB, iniA, or iniC genes. The mutant nucleic acid sequence may contain one or more deletions, insertions, substitutions, missense, nonsense, polymorphisms, point, or rearrangement mutations. The mutant nucleic acid sequence may be single-stranded, and labeled with a detectable marker.

Non-limiting examples of infections that can be treated using the methods of the present invention include those caused by mycobacteria selected from the group consisting of *Mycobacterium tuberculosis, Mycobacterium avium, Mycobacterium smegmatis, Mycobacterium bovis BCG, Mycobacterium leprae, Mycobacterium africanum,* and *Mycobacterium intracellulare.*

The nucleic acid sequences of the present invention are administered in conjunction with a suitable pharmaceutical carrier. Representative examples of suitable carriers include, but are not limited to, mineral oil, alum, and synthetic polymers. Vehicles for vaccines are well known in the art and the selection of a suitable vehicle is deemed to be within the scope of those skilled in the art from the teachings contained herein. The selection of a suitable vehicle is also dependent on the manner in which the nucleic acid sequences are to be administered. The nucleic acid sequences may be administered orally, enterally, subcutaneously, intraperitoneally, intravenously, or intranasally. Accordingly, as used herein, "subject" may be an embryo, fetus, newborn, infant, or adult. Further, as used herein "treating" is contacting a mycobacterium with the nucleic acids of the present invention, alone or in combination with other compositions.

The present invention additionally provides for the use of the nucleic acid sequences of the iniB, iniA, or iniC genes of the present invention as vaccines, or to improve existing vaccines.

Non-limiting examples of mycobacterial infections that can be treated using the vaccines of the present invention include those caused by mycobacteria selected from the group consisting of *Mycobacterium tuberculosis, Mycobacterium avium, Mycobacterium smegmatis, Mycobacterium bovis BCG, Mycobacterium leprae, Mycobacterium africanum,* and *Mycobacterium intracellulare.* For example, *M. tuberculosis* complex strains that have mutations in the iniB, iniA or iniC genes might have reduced virulence. In addition, mutated genes of *M. tuberculosis* and *M. bovis* can be added to BCG or tuberculosis vaccines to provide attenuated mutant tuberculosis vaccines. These vaccines can be used to treat and prevent a wide variety of diseases, including tuberculosis, human immunodeficiency viral infection, polio, leprosy, malaria, tetanus, diphtheria, influenza, measles, mumps, hepatitis and rabies.

The present invention also provides for novel vector constructs and a novel methods of using the constructs for screening drugs or compounds to determine whether the drug or compound is effective against *Mycobacterium tuberculosis.*

Specifically provided by the present invention are vector constructs comprising a DNA sequence comprising the iniB promoter region. The DNA encoding the iniB promoter region may be obtained several ways. For example, it can be prepared by isolating the iniB promoter region DNA sequences from a natural source, by synthesis using recombinant DNA techniques, by synthesis using a DNA synthesizer, or by amplification using the polymerase chain reaction. Such vectors may be constructed by inserting the DNA sequence comprising the iniB promoter region into a suitable vector. The term "inserted" as used herein means the ligation of a foreign DNA fragment and vector DNA by techniques such as the annealing of compatible cohesive ends generated by restriction endonuclease digestion or by use of blunt end ligation techniques. Other methods of ligating DNA molecules will be apparent to one skilled in the art.

Vectors suitable for expression of a DNA sequence comprising the iniB promoter region in a cell are well known to those skilled in the art and include pQE-8 (Qiagen), pET-3d (Novagen), pProEx-1 (Life Technologies), pFastBac 1 (Life Technologies), pSFV (Life Technologies), pcDNA II (Invitrogen), pSL301 (Invitrogen), pSE280 (Invitrogen), pSE380 (Invitrogen), pSE420 (Invitrogen), pTrcHis A,B,C (Invitrogen), pRSETA,B,C (Invitrogen), pYES2 (Invitrogen), pAC360 (Invitrogen), pVL1392 and pVl1392 (Invitrogen), pCDMB (Invitrogen), pcDNA 1 (Invitrogen), pcDNA I(amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), λPop6, pBR322, pUC18, pUC19, pHSV106, pJS97, pJS98, M13mp18, M13mp19, pSPORT 1, pGem, pSPORT 2, pSV SPORT 1, pBluescript II, λZapII, λgt10, λgt11, λgt22A, and λZIPLOX. Other vectors would be apparent to one skilled in the art.

The vector constructs of the present invention contain a nucleotide sequence encoding suitable regulatory elements so as to effect expression of the vector construct in a suitable host cell. Those skilled in the art will appreciate that a variety of enhancers, promoters, and genes are suitable for use in the constructs of the invention, and that the constructs will contain the necessary start, termination, ribosomal binding sequences, and control sequences for proper transcription and processing of the iniB promoter region when the vector construct is introduced into a host cell.

The vector constructs may contain one or more reporter genes. Examples of reporter genes that may be employed include, but are not limited to, luciferase from Vibrio or of firefly origin; green fluorescent protein; beta-galactosidase; beta-glucorindase; or catechol dehydrogenase and a strong mycobacterial promoter which controls expression of the reporter molecule-encoding gene. The reporter gene may be part of an existing vector, or it may be inserted during the course of the construction of the vector.

The vector constructs may also contain one or more expressible and selectable genes of interest. Examples of selectable markers that may be employed include, but are not limited to, leucine C, leucine D, chloramphenicol resistance gene, tetracycline resistance gene, hygromycin resistance gene, gentamycin resistance gene, B-galactosidase gene, ampicillin resistance gene, herpes simplex virus gene, vaccine virus thymidine kinase gene, adenine phosphoribosyltransferase gene, hypoxanthine-guanine phosphoribosyltransferase gene, aspartate transcarbamylase gene, ornithine decarboxylase gene, aminoglycoside phosphotransferase gene, hygromycin-B-phosphotransferase gene, xanthine-guanine phosphoribosyltransferase gene, tryptophan synthetase gene, histidinol dehydrogenase gene, multiple drug resistance gene, dihydrofolate reductase gene, CAD (carbamyl phosphate synthetase, aspartate transcarbamylase, and dihydroorotase) gene, adenosine deaminase gene, asparagine synthetase gene, and glutamine synthetase gene. The selectable marker may be part of an existing vector, or it may be inserted during the course of the construction of the vector.

The present invention further provides a cell transformed with the novel vector constructs of the present invention. The cell may be eukaryotic or prokaryotic. Suitable host cells include, but are not limited to, bacterial cells such as *E. coli, Bacillus subtilis, Agrobacterium tumefaciens, Bacillus subtilis, Agrobacterium tumefaciens, Bacillus megaterium*, eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator*, cultured insect cells, cultured chicken fibroblasts, cultured hamster cells, cultured human cells such as HT1080, MCF7, 143B and cultured mouse cells such as EL4 and NIH3T3 cells.

In a preferred embodiment of the invention, the cell transformed with the vector construct of the present invention is a mycobacterium. Non-limiting examples of mycobacterium which may be transformed with the vector construct of the present invention are *Mycobacterium tuberculosis, Mycobacterium avium, Mycobacterium smegmatis, Mycobacterium bovis BCG, Mycobacterium leprae, Mycobacterium africanum*, and *Mycobacterium intracellulare*.

The vector constructs of the present invention can exist in integrated or unintegrated form within the host cell and are capable of autonomous replication when in unintegrated form. The term "host cell" as used herein means the bacterial or eukaryotic cell into which the vector is introduced. As used herein, "introduced" is a general term indicating that one of a variety of means has been used to allow the vector to enter the intracellular environment of the host cell in such a way that it exists in stable form therein.

The constructs may be introduced into host cells by a variety of gene transfer methods known to those skilled in the art, such as electroporation, treatment with calcium chloride, DEAE dextran, cationic liposome fusion, protoplast fusion, DNA coated-microprojectile bombardment, and infection with recombinant replication-defective retroviruses. Other techniques will be obvious to one skilled in the art. The term "transformation" will be used herein as a general term to denote the introduction of vector into a bacterial or eukaryotic host cell. As such, it encompasses transformation of bacterial cells and transfection, transduction and related methods in eukaryotic cells.

The present invention also provides for the use of the vector constructs containing a DNA sequence comprising the iniB promoter region for screening drugs or compounds to determine whether the drug or compound is effective against *Mycobacterium tuberculosis*. This method comprises transforming the vector construct into a mycobacterium. Non-limiting examples of mycobacteria which may be used in this method include *Mycobacterium tuberculosis, Mycobacterium avium, Mycobacterium smegmatis, Mycobacterium bovis BCG, Mycobacterium leprae, Mycobacterium africanum*, and *Mycobacterium intracellulare*. The mycobacterium is cultured, preferably to an OD of 0.2–0.8. The drug or compound to be tested is then added to the culture and the mycobacteria are allowed to grow further. After a determined period of time, the culture is measured for induction of the iniB promoter. Induction is preferably determined by the expression of a reporter gene, such as lacZ or luciferase. Induction of the iniB promoter is a positive indication of the effectiveness of the drug or compound against the *Mycobacterium tuberculosis* cell wall and any other mechanism to be determined.

The present invention is described in the following Experimental Details Section, which is set forth to aid in an understanding of the invention, and should not be construed to limit in any way the invention as defined in the claims which follow thereafter.

EXPERIMENTAL DETAILS SECTION

Isolation and Identification of the iniB, iniA, and iniC Genes
  Libraries and plasmids.
  Cosmid libraries were constructed by ligation of Sau3A partial digests of *M. tuberculosis* H37Rv into pYUB328 (14). Plasmid libraries were constructed by ligation of complete PstI or SacI digests of *M. tuberculosis* H37Rv into pUC19 (15).

Creation of ribosomal free customized amplification libraries.

One thousand cosmid library clones were inoculated into "master" 96 well microtiter plates containing L broth and ampicillin 50 µg/ml, transferred by a pronged "frog" onto Biotrans nylon membranes (ICN Pharmaceuticals, Costa Mesa, Calif.), and hybridized separately with [$\alpha^{32}$P] radiolabled (Megaprime labeling kit, Amersham, Arlington Heights, Ill.) PCR probes to M. tuberculosis ribosomal 5S, 16S, and 23S genes. Fourteen cosmids containing ribosomal DNA were identified; non-ribosomal cosmids were re-inoculated from master plates and individually cultured. Cosmids were extracted by SDS/alkaline lysis (17) in pools of 16. Cosmid DNA was pooled, digested with PacI, which does not restrict the M. tuberculosis genome, and insert DNA was purified from an agarose gel by electro-elution. Approximately 1 µg of precipitated DNA was digested with AluI and 100 ng run on a 2% NuSieve GTG low melting point agarose gel (FMC Bioproducts, Rockland, Me.). Marker DNA was run simultaneously in a separate gel to avoid cross contamination of samples. The gels were aligned, and the section corresponding to 400–1,500 base pairs of the AluI digest was excised. Five µl of gel slice was ligated with 1 µl of Uniamp XhoI adapters 2 pmol/µl (Clonetech, Palo Alto, Calif.) in 20 µl total volume. Ten µl of the ligation was PCR amplified with 2 µl of 10 µM Uniamp primers (Clonetech), 1× vent polymerase buffer and 0.8 units of Vent (exo-) polymerase (New England Biolabs, Beverly, Mass.) in 100 µl total volume. After a five minute hot start, ten cycles of PCR with one minute segments of 95° C., 65° C., and 72° C., were followed by the addition of 3.2 units of Vent (exo-) polymerase and 27 additional cycles of 95° C. for one minute, 65° C. for two minutes, and 72° C. for three minutes. Uniamp primer sequence: 5'-CCTCTGAAGGTTCCAGAATCGATAG-3'(SEQ ID NO:6); Uniamp XhoI adapter sequence top strand: 5'-CCTC TGAAGGTTCCAGAATCGATAGCTCGAGT-3'(SEQ ID NO:7); bottom strand: 5'-P-ACTCGAGCTATCGATTC TGGAACCTTCAGAGGT-3'(SEQ ID NO:8).

RNA extraction.

Mycobacterial cultures were grown to mid log phase in Middlebrook 7H9 media supplemented with OADC, 0.05% Tween 80, and cyclohexamide (18) (for some experiments antibiotics were added for the last 18 hours), pelleted, resuspended in chloroform/methanol 3:1, and vortexed for 60 seconds or until the formation of an interface. RNA was extracted with five volumes of Triazole (Life Technologies, Gaithersburg, Md.), the aqueous layer precipitated in isopropanol, redissolved in 4M GTC and extracted a second time with Triazole.

Positive selection and generation of PCR probes.

One µg of RNA was reverse transcribed with 7.7 µg biotin labeled random hexamers and biotin dATP (one tenth total dATP) using superscript II (Gibco BRL, Grand Island, N.Y.) at 50° C. for one hour, RNAse H was then added for one half hour at 37° C. Three hundred ng of CAL, 20 µg of salmon sperm DNA, and 20 µg of tRNA were added to the cDNA for a final volume of 150 µl. The sample was phenol/chloroform extracted twice, ethanol precipitated overnight, resuspended in 6 µl of 30 mM EPPS (Sigma), pH 8.0/3 mM EDTA, overlain with oil, and heated to 99° C. for 5 minutes, then 1.5 µl of 5 M NaCl preheated to 69° C. was quickly added (19). The sample was incubated at 69° C. for three to four days, then diluted with 150 µl of incubation buffer (1×TE, 1 M NaCl, 0.5% Tween 20) that had been preheated to 69° C., and 50 µl of washed, preheated streptavadin coated magnetic beads (Dynal, Oslo, Norway) were then added. The sample was then incubated at 55° C. with occasional mixing for 30 minutes, washed three times at room temperature and three times 30 minutes at 69° C. with 0.1% SDS, 0.2× SSC by placing the microfuge tubes into a larger hybridization tube in a rotating microhybridization oven (Bellco, Vineland, N.J.). The sample was then washed with 2.5 mM EDTA and eluted by boiling in 80 µl of water. PCR was performed as in the CAL preparation using 20 µl of sample. The product of this PCR reaction is termed "PCR probes".

Colony array hybridizations.

Genomic plasmid library arrays were prepared by Genome Systems (St. Louis, Mo.) by robotically double spotting 9,216 colonies from the PstI and SacI plasmid libraries onto replicate nylon membranes. PCR probes were labeled by random priming with [$\alpha^{32}$P] dCTP (Megaprime labeling kit, Amersham) for at least 6 hours, hybridized to the colony arrays in Rapid-hyb buffer (Amersham), washed at 69° C. in 0.1× S. C., 0.1% SDS, and visualized by autoradiography. Double spotted colonies which hybridized at different intensities with two PCR probes were selected for further analysis.

Northern blots.

Five µg of each RNA sample were analyzed by northern blot with Northern Max kits (Ambion, Austin, Tex.) in a 1% denaturing agarose gel, probed with inserts of differentially expressed plasmids labeled by random priming with [$\alpha^{32}$P] dCTP, and visualized by autoradiography.

Southern blots.

Plasmid or genomic DNA was digested with restriction enzymes, subjected to electrophoresis in a 1% agarose gel and transferred by capillary action to Biotrans nylon membranes. The blots were hybridized and washed as in "colony array hybridizations" above, and visualized by autoradiography.

Reverse Transcription PCR.

Figure 2A:
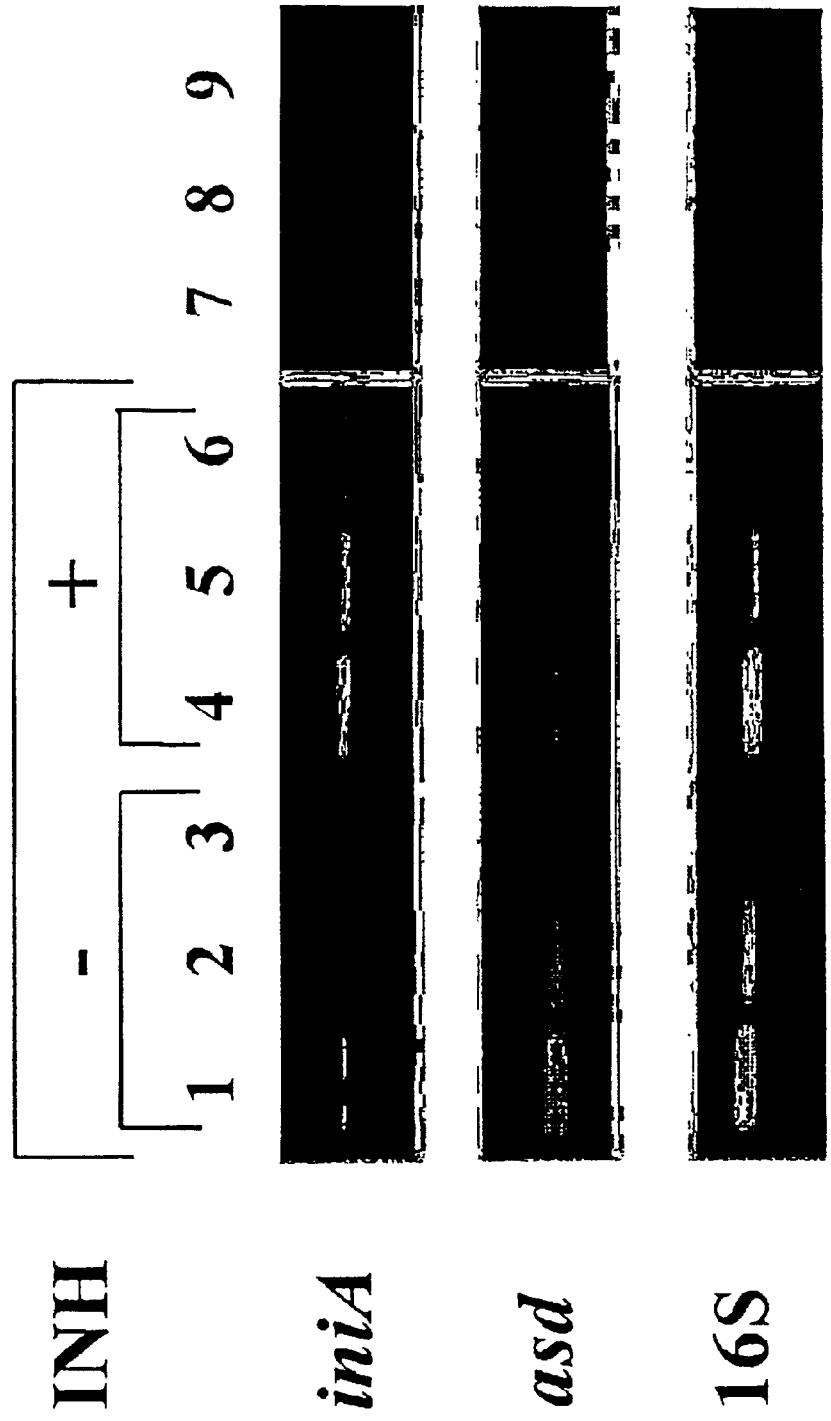
FIGS. 2A and 2B.
Figure 2B:
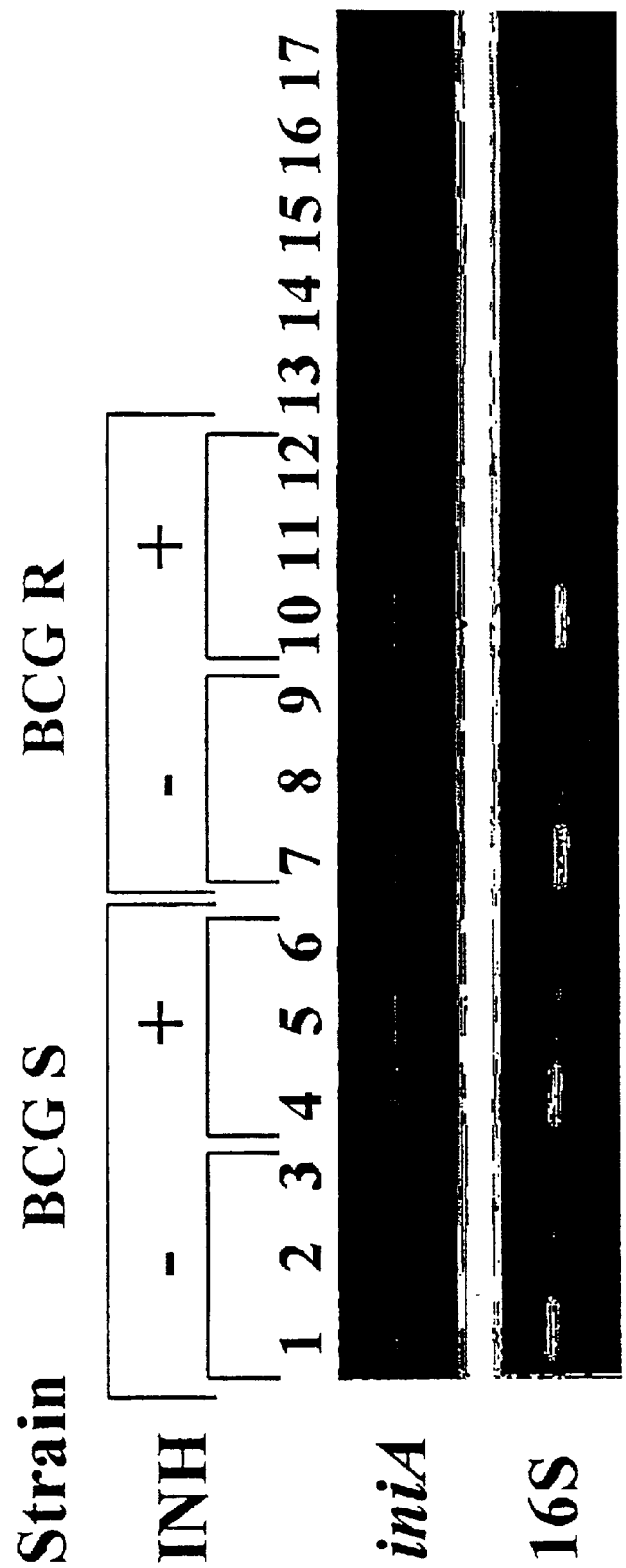

(See also FIG. 2) One microgram of RNA was reverse transcribed using the appropriate reverse PCR primer and superscript II at 50° C. For iniA and asd, three serial ten-fold dilutions of cDNA were made; 16S cDNA was diluted 1 in $10^6$, 1 in $10^7$, and 1 in $10^8$. PCR was performed with Taq polymerase and 1× PCR buffer (Gibco BRL) containing 2 mM $MgCl_2$ for 25 cycles annealing at 60° C. for iniA; 35 cycles annealing at 58° C. for asd; 25 cycles annealing at 63° C. for 16S. PCR products were analyzed on a 1.7% agarose gel, images were stored to disk by digital camera (Appligene, Pleasanton, Calif.), and the amounts of PCR product were calculated by densitometry (Imaging Software, National Institute of Health, Bethesda, Md. Primers used for iniA: 5'-GCGCTGGCGGGAGATCGTCAATG-3'(SEQ ID NO:9), 5'-TGCGCAGTCGGGTCACAGGAGTCG-3'(SEQ ID NO:10); for asd: 5'-TCCCGCCGCCGAACACCTA-3' (SEQ ID NO:11), 5'-GGATCCGGCCGACCAGAGA-3' (SEQ ID NO:12); for 16S: 5'-GGAGTACGGCCGCAA GGCTAAAAC-3'(SEQ ID NO:13), 5'-CAGACCCCGATC CGAACTGAGACC-3'(SEQ ID NO:14).

Induction of the iniB promoter.

The 213 base pair iniB promoter region was cloned into a lacZ and fflux reporter construct and transformed into BCG. Cells were cultured to an OD590 of 0.2–0.8 and then split into different aliquots. Individual aliquots of cells were treated with antibiotics, or other agents and cultured for an additional 24 and 48 hours. βgalactosidase activity of the culture was measured by an O-nitrophenyl β-D-galactopyranoside (ONPG) assay at various time points. Luciferase activity was measured by adding luciferase to the cultures and measuring relative light units in a luminometer.

Induction was calculated as the β-galactosidase or luciferase activity of antibiotic treated cells over β-galactosidase or luciferase activity of untreated control cultures at the same time point.

Induction of the iniB promoter by amino acids that block cell wall synthesis.

D-threonine, but not L-threonine inhibits cell wall biosynthesis by disrupting D-ala/D-ala cross-linking of the peptidoglycan cell wall. BCG containing the iniB/lacZ construct were treated with various antibiotics and amino acids. Induction of the iniB promoter at 24 hours with D-threonine is comparable to that of isoniazid and Unisyn (amoxicillin/sulbactam). Modest induction is also seen with 1% gylcine which is also known to weaken the mycobacterial cell wall. However, the L-threonine control did not cause induction.

Induction of the iniB promoter as a function of growth phase.

One BCG culture containing the iniA/lacZ construct was diluted in media to an OD590 of less than 0.1. The culture was placed at 37° C. with shaking. Two aliquots were removed from the culture at 24 hour intervals. Ethambutol was added to one aliquot; the second aliquot was used as a no antibiotics control. β-galactosidase activity was measured for both aliquots 24 hours later by ONPG assay and the process was repeated. β-galactosidase activity is shown for the un-treated control (squares), or ethambutol treated aliquot (diamonds) as a function of the $OD_{590}$ of the culture when the aliquots were removed (columns).

Use of the iniB promoter to screen compounds for new cell wall active drugs.

Mycobacteria, preferably M. tuberculosis but also other mycobacteria are transformed with a reporter construct under the control of the iniA promoter sequence as set forth in FIG. 6 or a smaller portion of this sequence, or a larger sequence. These transformed strains would be used to screen for compounds with cell wall activity either in liquid or solid phase assays. For testing using liquid phase assays, the transformed strains would be cultured to an OD of approximately 0.2 to 0.8 and then placed into microwell plates or other multiwell or multitube containers. Compounds to be tested would be added to each well, and the samples would be cultured for an additional period of time, usually between five and 48 hours. The growing strains could also be added to wells that already contained the compounds to be tested. These well would be cultured for similar periods of time. The wells would then be assayed for activity of the reporter molecule preferably luciferase or beta galactosidase. Compounds that caused significant induction of the iniB promoter would be identified by comparing the reporter activity in the wells containing the compounds to control wells to which either no compounds had been added, or to which suitable control compounds had been added. Significant induction would be any increase of the reporter in wells containing the test compounds over reporter activity in the control wells. Preferably the induction would be greater then two fold, more preferably it would be greater than five fold, and even more preferably it would be greater then tenfold. However, it might be determined that low levels of induction could indicate compounds with the potential to be modified for increased activity.

For solid phase assays.

The transformed strains are grown in agar or top agar and then compounds to be tested would be added on top of the growing strains. Compounds could be added to the agar using many methods, for example the compounds could be contained in small particles that would be dropped onto the agar in defined arrays. Induction of the promoter would be identified by a color change or other change in the media surrounding the compound, for example due to beta galactosidase activity.

B. Results

Detection and evaluation of differential gene expression.

Differentially expressed genes were determined by examining the differential hybridization patterns of the PCR probes referred to in Materials and Methods: Positive seclection and geberation of PCR probes. PCR probes derived from INH− and INH+ RNA samples were radiolabeled and hybridized to replica membranes containing arrays of colonies from an M. tuberculosis genomic library. Hybridization signals to most colonies were equal when small differences in background were accounted for, but a subset of colonies was found to hybridize more strongly to either the INH− or INH+ probe. Six colonies were selected for further evaluation; five hybridized more strongly with the INH+ probe (P1–P5) and one hybridized more strongly with the INH− probe (P6). Differential hybridization was confirmed for P1, P2, P3, and P6 by re-hybridizing the INH− and INH+ PCR probes to duplicate Southern blots of the excised plasmid inserts. P1 and P6 hybridized almost exclusively to the appropriate of the PCR probes, while P2 and P3 hybridized to both probes but with different intensities. P4 and P5 were found not to hybridize differentially on secondary screen. The ends of the plasmid inserts were sequenced and aligned to the completely sequenced M. tuberculosis genome (20). P1 and P2, which encoded sequences that hybridized almost exclusively with the INH+ probe were homologous to a set of predicted proteins. P1 encoded a sequence identical to Rv0342, a large open reading frame that appeared to be the second gene of a probable three gene operon. This open reading frame was named iniA (isoniazid induced gene A), and the upstream open reading frame Rv0341, was named iniB. P2 encoded a sequence that was not complementary to P1, but that was identical to the third gene in the same probable operon Rv0343, this open reading frame was named iniC. A putative protein encoded by the iniA gene was found to contain a phosphopantetheine attachment site motif (21) suggesting that it functions as an acyl carrier protein. Both iniA and iniC lacked significant homology to other known genes but were 34% identical to each other. A sequence similarity search demonstrated that iniB had weak homology to alanine-glycine rich cell wall structural proteins (22). Northern blot analysis using excised inserts to probe total RNA from M. tuberculosis cultured in the presence or absence or different antibiotics verified that iniA was strongly induced by isoniazid and ethambutol, drugs that act by inhibiting cell wall biosynthesis but not by rifampin or streptomycin, agents that do not act on the cell wall (FIG. 1). P3, which also encoded a sequence that preferentially hybridized to the INH+ probe contained a 5 kb insert spanning M. tuberculosis cosmids MTCYH10 and MTCY21D4. This region contained multiple small open reading frames, most with no known function. Northern blot analysis using the 5 kb insert as a probe confirmed that P3 preferentially hybridized to RNA from M. tuberculosis that had been cultured in the presence of isoniazid (data not shown). P6, which encoded a sequence hybridizing predominanty with the INH− probe was found to encode L-aspartic-β-semialdehyde dehydrogenase (asd). The asd gene is an important component of the diaminopimelate pathway required for biosynthesis of the peptidoglycan component of bacterial cell walls. Modulation of asd by a cell wall antibiotic such as isoniazid is not unexpected.

Reverse transcription (RT) PCR assays confirmed differential gene expression of both asd and iniA (FIG. 2A), as well as of iniB and iniC (data not shown). As predicted, iniA was strongly induced by isoniazid (70 fold induction by densitometry), while asd was repressed (17 fold). Induction of iniA was also tested in two isogenic strains of BCG that were either sensitive or resistant to isoniazid. The resistant phenotype was conferred by a mutation in katG which normally converts isoniazid from a prodrug to its active form (23). Induction of iniA was seen only in the susceptible BCG strain demonstrating the requirement for isoniazid activation.

C. Discussion

Figure 3:
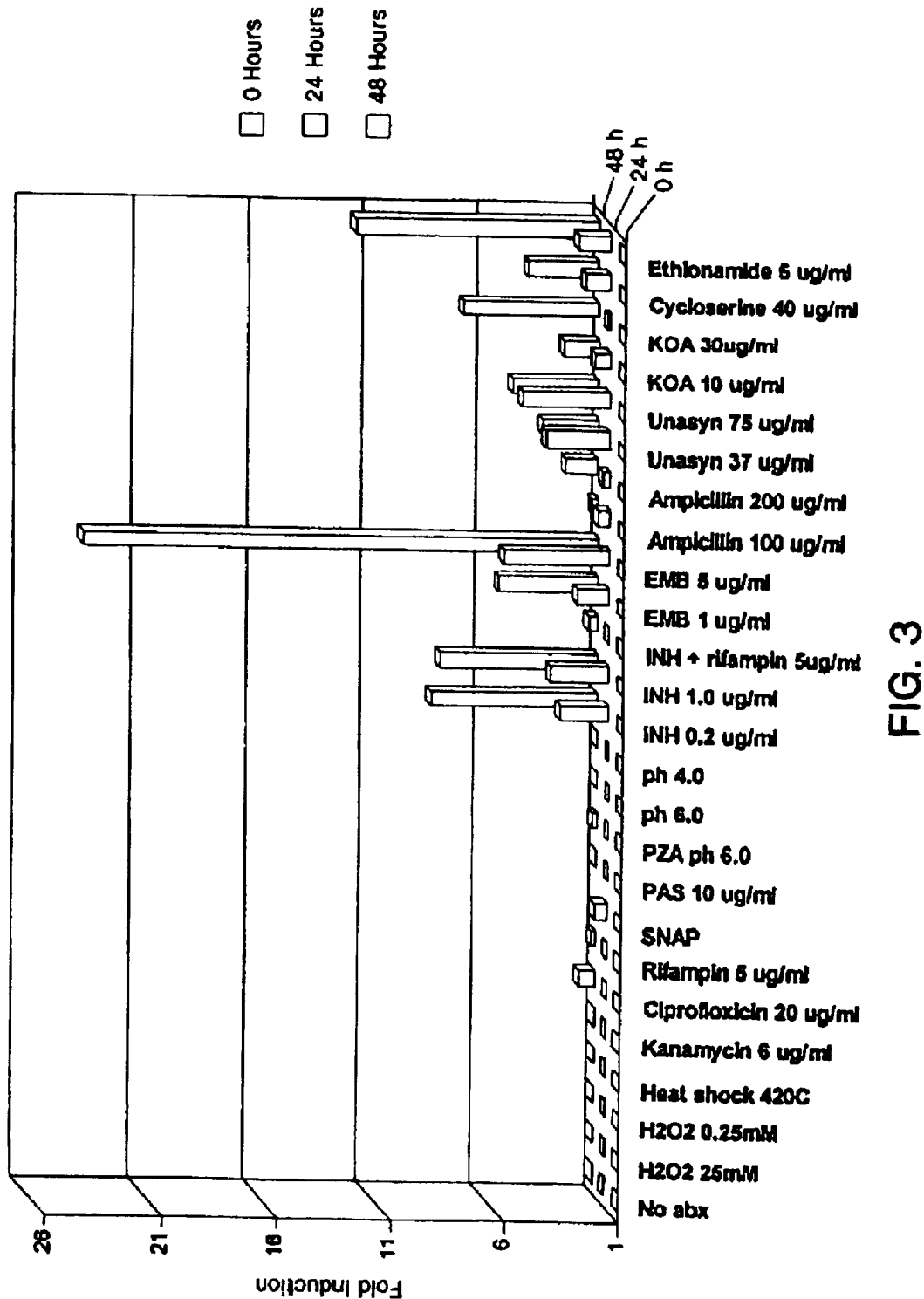
FIG. 3.
Figure 4:
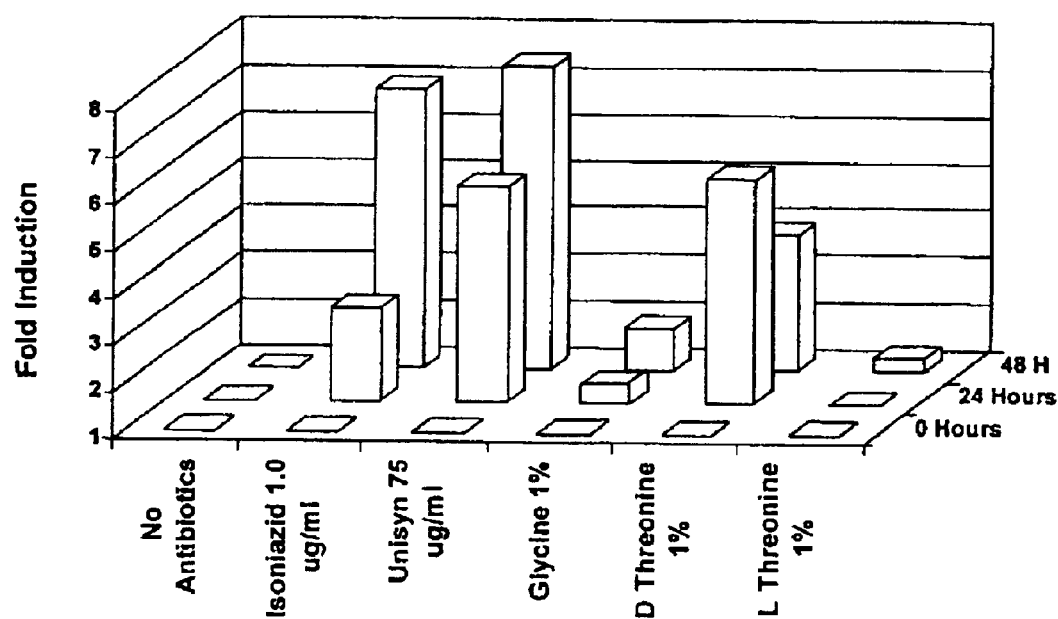
FIG. 4.

A three gene operon (the iniA operon) was discovered in M. tuberculosis that was strongly induced by both isoniazid and ethambutol. A 213 base pair sequence containing the iniB promoter was cloned into a lacz reporter construct. Using this construct, it is herein demonstrated that the iniB promoter is induced by a wide range of cell wall active compounds but not by antibiotics or other stresses that do not act on the cell wall (FIG. 3 and FIG. 5). The iniB promoter is induced by antibiotics that act on very different targets within the cell wall including isoniazid which inhibits mycolic acid biosynthesis, EMB which inhibits arabinan and lipoarabinomannan biosynthesis, cycloserine which inhibits peptidoglycan cross linking and amoxicillin/sulbactam which inhibits penicillin binding proteins. The iniA gene is also induced by D-threonine, an amino acid that substitutes for D-alanine and inhibits peptidoglycan biosynthesis. In contrast, L-threonine has a minimal effect on iniA transcription (FIG. 4). The induction is not an artifact of cell wall breakdown and increased release of the β-galactosidase reporter because iniB promoter induction can be reversed by co-administration of the RNA polymerase inhibitor rifampin (FIG. 3). Induction has been demonstrated only during log phase growth of the recombinant BCG strain containing the reporter construct (FIG. 5). This may be due to the intrinsic property of the promoter but may also reflect the mechanisms of action of the antibiotics available for testing. It is possible that the iniA promoter is also inducible in stationary phase. This hypothesis would need to be tested with a compound that was able to disrupt cell wall biosynthesis during the stationary phase of the cell cycle.

The iniB promoter may be used in a reporter construct to rapidly screen compounds for new cell wall active drugs. Screening for iniB promoter induction would also permit drugs to be assayed at higher than normal concentrations because it will be possible to distinguish between cell wall activity and nonspecific effects on cell growth. If the iniB promoter is inducible during stationary phase, then this strategy could be used to discover drugs that could be effective on latent or persistent infections.

While the foregoing invention has been described in detail for purpose of clarity and understanding, it will be appreciated by one skilled in the art from a reading of the disclosure that various changes in form and detail can be made without departing from the true scope of the invention in the appended claims.

REFERENCES

1. Sanders, C. C. (1987) *Annu. Rev. Microbiol.* 41, 573–593.
2. Miller, J. F., Mekalanos, J. J., & Falkow, S. (1989) *Science* 243, 916–922.
3. Korfmann, G., Sanders, C. C ., & Morland, E. S. (1991) *Antibicrob. Agents Chemother.* 35, 358–364.
4. Beattie, D. T., Shahin, R., & Mekalanos, J. J. (1992) *Infect. Immun.* 60, 571–577.
5. Stragier, P., & Losick, R. (1996) *Annu. Rev. Genet.* 30, 297–341.
6. Mathiopoulos, C., & Sonenshein, A. L. (1989) *Mol. Microbiol.* 3,1071–1081.
7. Wang, Z., & Brown, D. D. (1991) *Proc. Natl. Acad. Sci. USA* 88, 11505–11517.
8. Kinger, K. A., & Tyagi, J. S. (1993) *Gene* 131, 113–117.
9. Plum, G., & Clark-Curtis, J. E. (1994) *Infect. and Immun.* 62, 476–483.
10. Wong, K. K., & McClelland, M. (1994) *Proc. Natl. Acad. Sci. USA* 91, 639–643.
11. Utt, E. A., Brousal, J. P., Kikuta-Oshima, L. C., & Quinn, F. D. (1995) *Can. J. Microbiol.* 41, 152–156.
12. de Saizieu, A., Certa, U., Warrington, J., Gray, C., Keck, W., & Mous, J. (1998) *Nature Biotech.* 16, 45–48.
13. Marshall, A., & Hodgson, J. (1998) *Nature Biotech.* 16, 27–31.
14. Balasubramanian, V., Pavelka, M. S., Jr., Bardarov, S. S., Martin, J., Weisbrod, T. R., McAdam, R. A, Bloom, B. R., & Jacobs, W. R., Jr. (1996) *J. Bacteriol.* 178, 273–279.
15. Miller, L. P., Crawford, J. T., & Shinnick, T. M. (1994) *Antibicrob. Agents Chemother.* 38, 805–811.
16. Cirillo, J. D., Weisbrod, T. R., Pascopella, L., Bloom, B. R., & Jacobs, W. R., Jr. (1994) *Mol. Microbiol.* 11, 629–639.
17. Maniatis, T., Fritsch, E. F., & Sambrook, J. (1989) *Molecular Cloning: a Laboratory Manual* (Cold Spring Harbor Lab. Press, Cold Spring Harbor, N.Y.), $2^{nd}$ ed.
18. Jacobs, W. R., Kalpana, G. V., Cirillo, J. D., Pascopella, L., Snapper, S. B., Udani, R. A., Jones, W., Barletta, R. G., & Bloom, B. R. (1991) 204, 537–555.
19. Lisitsyn, N., Lisitsyn, N., & Wigler, M. (1993) *Science* 259, 946–951.
20. Cole, S. T., Brosch, R., Parkhill, J., Gamier, T., Churcher, C., Harris, D., Gordon, S. V., Eiglmeier, L., Gas, S., et al. (1998) *Nature* 393, 537–544.
21. Bairoch, A., Bucher, P., & Hofmann, K. (1997) *Nucleic Acids Res.* 25, 217–221.
22. Altschul, S. F., Madden, T. L., Schaffer, A. A., Zhang, J., Zhang, Z., Miller, W., & Lipman, D. J. (1997) *Nucleic Acids Res.* 25, 3389–3402.
23. Zhang, Y., Heym, B., Allen, B., Young, D., & Cole, S. (1992) *Nature* 358, 591–593.
24. Bass, J. B., Jr., Farer, L. S., Hopewell, P. C., O'Brien, R., Jacobs, R. F., Ruben, F., Snider, D. E., Jr., & Thornton, G. (1994) *Am. J. Respir. Crit. Care. Med.* 149, 1359–1374.
25. Banedee, A., Dubnau, E., Quemard, A., Balasubramanian, V., Um, K. S., Wilson, T., Collins, D., de Lisle, G., Jacobs, W. R., Jr. (1994) *Science* 263, 227–230.
26. Mdluli, K., Slayden, R. A., Zhu, Y., Ramaswamy, S., Pan, X., Mead, D., Crane, D. D., Musser, M. J., & Barry, C. E., III. (1998) *Science.* 280, 1607–1610.
27. Belanger, A. E., Besra, G. S., Ford, M. E., Mikusova, K, Belisle, J. T., Brennan, P. J., Inamine, J. M. (1996) *Proc. Natl. Acad. Sci. USA* 93, 11919–11924.
28. Telenti, A., Philipp, W. J., Sreevatsan, S., Bernasconi, C., Stockbauer, K. E., Wieles, B., Musser, J. M., Jacobs, W. R., Jr. (1997) *Nat. Med.* 3, 567–570.
29. Garbe, T. R., Hibler, N. S., & Deretic, V. (1996) 40, 1754–1756.

What is claimed is:

1. A method of determining whether a drug or compound is effective against *Mycobacterium tuberculosis* comprising:
   (a) transforming a mycobacterium with a vector construct comprising a *Mycobacterium tuberculosis* iniB promoter inserted into a plasmid;
   (b) culturing the *Mycobacterium*;
   (c) treating the cultured *Mycobacterium* with the drug; and
   (d) measuring induction of the iniB promoter, wherein the induction of the iniB promoter causes expression of a reporter gene, and wherein the presence of induction indicates the drug is effective against *Mycobacterium tuberculosis*.

2. The method of claim 1, wherein the *Mycobacterium* is selected from the group consisting of *Mycobacterium tuberculosis, Mycobacterium avium, Mycobacterium smegmatis, Mycobacterium bovis BCG, Mycobacterium leprae, Mycobacterium africanium*, and *Mycobacterium intracellulare*.

3. The method of claim 1, wherein the reporter gene is selected from the group consisting of lacZ and luciferase.

4. The method of claim 1, wherein the drug or compound is effective against the biosynthesis of the *Mycobacterium tuberculosis* cell wall.

5. The method of claim 1, wherein the nucleotide sequence of the iniB promoter comprises SEQ ID NO:1 and nucleotides 1–159 of SEQ ID No:2.

* * * * *

SEQUENCE LISTING

<160> NUMBER OF SEQ ID NOS: 14

<210> SEQ ID NO 1
<211> LENGTH: 53
<212> TYPE: DNA
<213> ORGANISM: Mycobacterium tuberculosis

<400> SEQUENCE: 1
cacggctacg acatccacgg ataagttccg gaccggcgta ggggtgcccc att        53

<210> SEQ ID NO 2
<211> LENGTH: 5036
<212> TYPE: DNA
<213> ORGANISM: Mycobacterium tuberculosis

<400> SEQUENCE: 2

| | | | | | |
|---|---|---|---|---|---|
| tcccctaatc | ccctaacgcg | gcggccaggc | cgatcccgat | aggtgtttgg | ccggcttgcg | 60 |
| gatcagaccc | cgatttcggg | gtgaggcgga | atccatagcg | tcgatggcac | agcgccggtc | 120 |
| acgccggcga | acagcttctt | cgattgaagg | gaaatgaaga | tgacctcgct | tatcgattac | 180 |
| atcctgagcc | tgttccgcag | cgaagacgcc | gcccggtcgt | tcgttgccgc | tccgggacgg | 240 |
| gccatgacca | gtgccgggct | gatcgatatc | gcgccgcacc | aaatctcatc | ggtgccggcc | 300 |
| aatgtggtgc | cgggtctgaa | tctgggtgcc | ggcgacccca | tgagcggatt | gcggcaggcc | 360 |
| gtcgccgctc | ggcatggctt | tgcgcaggac | gtcgccaatg | tcggcttcgc | cggtgacgcg | 420 |
| ggcgcggggg | tggcaagcgt | catcacgacc | gatgtcggtg | cgggcctggc | tagcggactg | 480 |
| ggtgctgggt | tcctgggtca | gggtggcctg | gctctcgccg | cgtcaagcgg | tggtttcggc | 540 |
| ggtcaggtcg | gcttggctgc | ccaggtcggt | ctgggtttta | ctgccgtgat | tgaggccgag | 600 |
| gtcggcgctc | aggttggtgc | tgggttaggt | attgggacgg | gtctgggtgc | tcaggccggt | 660 |
| atgggctttg | gcggcggggt | tggcctgggt | ctgggtggtc | aggccggcgg | tgtgatcggt | 720 |
| gggagcgcgg | ccggggctat | cggtgccggc | gtcggcggtc | gcctaggcgg | caatggccag | 780 |
| atcggagttg | ccggccaggg | tgccgttggc | gctggtgtcg | gcgctggtgt | cggcggccag | 840 |
| gcgggcatcg | ctagccagat | cggtgtctca | gccggtggtg | ggctcggcgg | cgtcggcaat | 900 |
| gtcagcggcc | tgaccggggt | cagcagcaac | gcagtgttgg | cttccaacgc | aagcggccag | 960 |
| gcggggttga | tcgccagtga | aggcgctgcc | ttgaacggcg | ctgctatgcc | tcatctgtcg | 1020 |
| ggcccgttag | ccggtgtcgg | tgtgggtggt | caggccggcg | ccgctggcgg | cgccgggttg | 1080 |
| ggcttcggag | cggtcgggca | cccgactcct | cagccggcgg | ccctgggcgc | ggctggcgtg | 1140 |
| gtggccaaga | ccgaggcggc | tgctggagtg | gttggcgggg | tcggcggggc | aaccgcggcc | 1200 |
| ggggtcggcg | gggcacacgg | cgacatcctg | ggccacgagg | gagccgcact | gggcagtgtc | 1260 |
| gacacggtca | acgccggtgt | cacgcccgtc | gagcatggct | tggtcctgcc | cagtggcccc | 1320 |
| ctgatccacg | gcggtaccgg | cggctatggc | ggcatgaacc | cgccagtgac | cgatgcgccg | 1380 |
| gcaccgcaag | ttccggcgcg | ggcccagccg | atgaccacgg | cggccgagca | cacgccggcg | 1440 |
| gttacccaac | cgcagcacac | gccggtcgag | ccgccggtcc | acgataagcc | gccgagccat | 1500 |
| tcggtgtttg | acgtcggtca | cgagccgccg | gtgacgcaca | cgccgccggc | gcccatcgaa | 1560 |
| ctgccgtcgt | acggcctttt | cggactaccc | gggttctgat | tcgcgagccg | atttcacgaa | 1620 |
| ccggtgggga | cgttcatggt | ccccgccggt | ttgtgcgcat | accgtgatct | gaggcgtaaa | 1680 |
| cgagcgagaa | agtggggcga | cacggtgacc | cagcccgatg | acccacgtcg | ggtcggtgtg | 1740 |

```
atcgtcgaac tgatcgatca cactatcgcc atcgccaaac tgaacgagcg tggtgatcta    1800
gtacagcggt tgacgcgggc tcgccagcgg atcaccgacc cgcaggtccg tgtggtgatc    1860
gccgggctgc tcaaacaggg caagagtcaa ttgctcaatt cgttgctcaa cctgcccgcg    1920
gcgcgagtag gcgatgacga ggccaccgtg gtgatcaccg tcgtaagcta cagcgcccaa    1980
ccgtcggccc ggcttgtgct ggccgccggg cccgacggga caaccgcagc ggttgacatt    2040
cccgtcgatg acatcagcac cgatgtgcgt cgggctccgc acgccggtgg ccgcgaggtg    2100
ttgcgggtcg aggtcggcgc gcccagcccg ctgctgcggg gcgggctggc gtttatcgat    2160
actccgggtg tgggcggcct cggacagccc cacctgtcgg cgacgctggg gctgctaccc    2220
gaggccgatg ccgtcttggt ggtcagcgac accagccagg aattcaccga acccgagatg    2280
tggttcgtgc ggcaggccca ccagatctgt ccggtcgggg cggtcgtggc caccaagacc    2340
gacctgtatc cgcgctggcg ggagatcgtc aatgccaatg cagcacatct gcagcgggcc    2400
cgggttccga tgccgatcat cgcagtctca tcactgttgc gcagccacgc ggtcacgctt    2460
aacgacaaag agctcaacga agagtccaac tttccggcga tcgtcaagtt tctcagcgag    2520
caggtgcttt cccgcgcgac ggagcgagtg cgtgctgggg tactcggcga aatacgttcg    2580
gcaacagagc aattggcggt gtctctaggt tccgaactat cggtggtcaa cgacccgaac    2640
ctccgtgacc gacttgcttc ggatttggag cggcgcaaac gggaagccca gcaggcggtg    2700
caacagacag cgctgtggca gcaggtgctg ggcgacgggt tcaacgacct gactgctgac    2760
gtggaccacg acctacgaac ccgcttccgc accgtcaccg aagacgccga cgccagatc     2820
gactcctgtg acccgactgc gcattgggcc gagattggca acgacgtcga aatgcgatc     2880
gccacagcgg tcggcgacaa cttcgtgtgg gcataccagc gttccgaagc gttggccgac    2940
gacgtcgctc gctcctttgc cgacgcgggg ttggactcgg tcctgtcagc agagctgagc    3000
ccccacgtca tgggcaccga cttcggccgg ctcaaagcgc tgggccggat ggaatcgaaa    3060
ccgctgcgcc ggggccataa aatgattatc ggcatgcggg gttcctatgg cggcgtggtc    3120
atgattggca tgctgtcgtc ggtggtcgga cttgggttgt tcaacccgct atcggtgggg    3180
gccgggttga tcctcggccg gatggcatat aaagaggaca acaaaaccg gttgctgcgg     3240
gtgcgcagcg aggccaaggc caatgtgcgg cgcttcgtcg acgacatttc gttcgtcgtc    3300
agcaaacaat cacgggatcg gctcaagatg atccagcgtc tgctgcgcga ccactaccgc    3360
gagatcgccg aagagatcac ccgtcgctc accgagtccc tgcaggcgac catcgcggcg     3420
gcgcaggtgg cggaaaccga gcgggacaat cgaattcggg aacttcagcg gcaattgggt    3480
atcctgagcc aggtcaacga caaccttgcc ggcttggagc caaccttgac gccccggggcg   3540
agcttgggac gagcgtgagc accagcgacc gggtccgcgc gattctgcac gcaaccatcc    3600
aggcctaccg gggtgcgccg gcctatcgtc agcgtggcga cgttttttgc cagctggacc    3660
gcatcggtgc gcgcctagcc gaaccgctgc gcatcgcgtt ggctggcaca ctcaaggccg    3720
gaaaatccac tctcgtcaac gcccttgtcg gcgacgacat cgctccgacc gatgccaccg    3780
aggccacccg gattgtgacc tggttccggc acggtccgac accgcgggtc accgccaacc    3840
atcgcggcgg tcgacgcgcc aacgtgccga tcacccgtcg gggcgggctg agtttcgacc    3900
tgcgcaggat caacccggcc gagctgatcg acctggaagt cgagtggcca gccgaggaac    3960
tcatcgacgc caccattgtt gacaccccgg gaacgtcgtc gttggcatgc gatgcctccg    4020
agcgcacgtt gcggctgctg gtccccgccg acggggtgcc tcgggtggat gcggtggtgt    4080
```

-continued

```
tcctgttgcg cacccctgaac gccgctgacg tcgcgctgct caaacagatc ggtgggctgg      4140
tcggcgggtc ggtgggagcc ctgggcatca tcggggtggc gtctcgcgcg gatgagatcg      4200
gcgcgggccg catcgacgcg atgctctcgg ccaacgacgt ggccaagcgg ttcacccgcg      4260
aactgaacca gatgggcatt tgccaggcgg tggtgccggt atccggactt cttgcgctga      4320
ccgcgcgcac actgcgccag accgagttca tcgcgctgcg caagctggcc ggtgccgagc      4380
gcaccgagct caatagggcc ctgctgagcg tggaccgttt tgtgcgccgg acagtccgc       4440 taccggtgga cgcgggcatc cgtgcgcaat tgctcgagcg gttcggcatg ttcggcatcc      4500
ggatgtcgat tgccgtgctg gcggccggcg tgaccgattc gaccgggctg ccgccgaac       4560 tgctggagcg cagcgggctg gtggcgctgc gcaatgtgat agaccagcag ttcgcgcagc      4620
gctccgacat gcttaaggcg cataccgcct tggtctcctt gcgccgattc gtgcagacgc      4680
atccggtgcc ggcgaccccg tacgtcattg ccgacatcga cccgttgcta gccgacaccc      4740
acgccttcga agaactccga atgctaagcc ttttgccttc gcgggcaacg acattgaacg      4800
acgacgaaat cgcgtcgctg cgccgcatca tcggcgggtc gggcaccagt gccgccgctc      4860
ggctgggcct ggatcccgcg aattctcgcg aggccccgcg cgccgcgctg ccgcagcgc       4920 aacactggcg tcgccgtgcg gcgcatccac tcaacgatcc gttcactacc agggcctgtc      4980
gcgcggcggt gcgcagcgcc gaggcgatgg tggcggagtt ctctgctcgc cgctga         5036
```

<210> SEQ ID NO 3
<211> LENGTH: 479
<212> TYPE: PRT
<213> ORGANISM: Mycobacterium tuberculosis

<400> SEQUENCE: 3

```
Met Thr Ser Leu Ile Asp Tyr Ile Leu Ser Leu Phe Arg Ser Glu Asp
  1               5                  10                  15

Ala Ala Arg Ser Phe Val Ala Ala Pro Gly Arg Ala Met Thr Ser Ala
             20                  25                  30

Gly Leu Ile Asp Ile Ala Pro His Gln Ile Ser Ser Val Ala Ala Asn
         35                  40                  45

Val Val Pro Gly Leu Asn Leu Gly Ala Gly Asp Pro Met Ser Gly Leu
     50                  55                  60

Arg Gln Ala Val Ala Ala Arg His Gly Phe Ala Gln Asp Val Ala Asn
 65                  70                  75                  80

Val Gly Phe Ala Gly Asp Ala Gly Ala Gly Val Ala Ser Val Ile Thr
                 85                  90                  95

Thr Asp Val Gly Ala Gly Leu Ala Ser Gly Leu Gly Ala Gly Phe Leu
            100                 105                 110

Gly Gln Gly Gly Leu Ala Leu Ala Ala Ser Ser Gly Gly Phe Gly Gly
        115                 120                 125

Gln Val Gly Leu Ala Ala Gln Val Gly Leu Gly Phe Thr Ala Val Ile
    130                 135                 140

Glu Ala Glu Val Gly Ala Gln Val Gly Ala Gly Leu Gly Ile Gly Thr
145                 150                 155                 160

Gly Leu Gly Ala Gln Ala Gly Met Gly Phe Gly Gly Val Gly Leu
                165                 170                 175

Gly Leu Gly Gly Gln Ala Gly Gly Val Ile Gly Gly Ser Ala Ala Gly
            180                 185                 190

Ala Ile Gly Ala Gly Val Gly Gly Arg Leu Gly Gly Asn Gly Gln Ile
        195                 200                 205
```

-continued

Gly Val Ala Gly Gln Gly Ala Val Gly Ala Gly Val
        210                 215                 220

Gly Gly Gln Ala Gly Ile Ala Ser Gln Ile Gly Val Ser Ala Gly Gly
225                 230                 235                 240

Gly Leu Gly Gly Val Gly Asn Val Ser Gly Leu Thr Gly Val Ser Ser
                245                 250                 255

Asn Ala Val Leu Ala Ser Asn Ala Ser Gly Gln Ala Gly Leu Ile Ala
            260                 265                 270

Ser Glu Gly Ala Ala Leu Asn Gly Ala Ala Met Pro His Leu Ser Gly
        275                 280                 285

Pro Leu Ala Gly Val Gly Val Gly Gly Gln Ala Gly Ala Ala Gly Gly
    290                 295                 300

Ala Gly Leu Gly Phe Gly Ala Val Gly His Pro Thr Pro Gln Pro Ala
305                 310                 315                 320

Ala Leu Gly Ala Ala Gly Val Val Ala Lys Thr Glu Ala Ala Ala Gly
                325                 330                 335

Val Val Gly Gly Val Gly Gly Ala Thr Ala Ala Gly Val Gly Gly Ala
            340                 345                 350

His Gly Asp Ile Leu Gly His Glu Gly Ala Ala Leu Gly Ser Val Asp
        355                 360                 365

Thr Val Asn Ala Gly Val Thr Pro Val Glu His Gly Leu Val Leu Pro
    370                 375                 380

Ser Gly Pro Leu Ile His Gly Thr Gly Gly Tyr Gly Gly Met Asn
385                 390                 395                 400

Pro Pro Val Thr Asp Ala Pro Ala Pro Gln Val Pro Ala Arg Ala Gln
                405                 410                 415

Pro Met Thr Thr Ala Ala Glu His Thr Pro Ala Val Thr Gln Pro Gln
            420                 425                 430

His Thr Pro Val Glu Pro Pro Val His Asp Lys Pro Pro Ser His Ser
        435                 440                 445

Val Phe Asp Val Gly His Glu Pro Pro Val Thr His Thr Pro Pro Ala
    450                 455                 460

Pro Ile Glu Leu Pro Ser Tyr Gly Leu Phe Gly Leu Pro Gly Phe
465                 470                 475

<210> SEQ ID NO 4
<211> LENGTH: 640
<212> TYPE: PRT
<213> ORGANISM: Mycobacterium tuberculosis

<400> SEQUENCE: 4

Met Val Pro Ala Gly Leu Cys Ala Tyr Arg Asp Leu Arg Arg Lys Arg
1               5                   10                  15

Ala Arg Lys Trp Gly Asp Thr Val Thr Gln Pro Asp Pro Arg Arg
            20                  25                  30

Val Gly Val Ile Val Glu Leu Ile Asp His Thr Ile Ala Ile Ala Lys
        35                  40                  45

Leu Asn Glu Arg Gly Asp Leu Val Gln Arg Leu Thr Arg Ala Arg Gln
    50                  55                  60

Arg Ile Thr Asp Pro Gln Val Arg Val Ile Ala Gly Leu Leu Lys
65                  70                  75                  80

Gln Gly Lys Ser Gln Leu Leu Asn Ser Leu Leu Asn Leu Pro Ala Ala
                85                  90                  95

Arg Val Gly Asp Asp Glu Ala Thr Val Val Ile Thr Val Ser Tyr
            100                 105                 110

-continued

```
Ser Ala Gln Pro Ser Ala Arg Leu Val Leu Ala Ala Gly Pro Asp Gly
        115                 120                 125
Thr Thr Ala Ala Val Asp Ile Pro Val Asp Asp Ile Ser Thr Asp Val
    130                 135                 140
Arg Arg Ala Pro His Ala Gly Gly Arg Glu Val Leu Arg Val Glu Val
145                 150                 155                 160
Gly Ala Pro Ser Pro Leu Leu Arg Gly Leu Ala Phe Ile Asp Thr
                165                 170                 175
Pro Gly Val Gly Gly Leu Gly Gln Pro His Leu Ser Ala Thr Leu Gly
                180                 185                 190
Leu Leu Pro Glu Ala Asp Ala Val Leu Val Ser Asp Thr Ser Gln
        195                 200                 205
Glu Phe Thr Glu Pro Glu Met Trp Phe Val Arg Gln Ala His Gln Ile
    210                 215                 220
Cys Pro Val Gly Ala Val Val Ala Thr Lys Thr Asp Leu Tyr Pro Arg
225                 230                 235                 240
Trp Arg Glu Ile Val Asn Ala Asn Ala Ala His Leu Gln Arg Ala Arg
                245                 250                 255
Val Pro Met Pro Ile Ile Ala Val Ser Ser Leu Leu Arg Ser His Ala
                260                 265                 270
Val Thr Leu Asn Asp Lys Glu Leu Asn Glu Glu Ser Asn Phe Pro Ala
        275                 280                 285
Ile Val Lys Phe Leu Ser Glu Gln Val Leu Ser Arg Ala Thr Glu Arg
    290                 295                 300
Val Arg Ala Gly Val Leu Gly Glu Ile Arg Ser Ala Thr Glu Gln Leu
305                 310                 315                 320
Ala Val Ser Leu Gly Ser Glu Leu Ser Val Val Asn Asp Pro Asn Leu
                325                 330                 335
Arg Asp Arg Leu Ala Ser Asp Leu Glu Arg Arg Lys Arg Glu Ala Gln
                340                 345                 350
Gln Ala Val Gln Gln Thr Ala Leu Trp Gln Gln Val Leu Gly Asp Gly
        355                 360                 365
Phe Asn Asp Leu Thr Ala Asp Val Asp His Asp Leu Arg Thr Arg Phe
    370                 375                 380
Arg Thr Val Thr Glu Asp Ala Glu Arg Gln Ile Asp Ser Cys Asp Pro
385                 390                 395                 400
Thr Ala His Trp Ala Glu Ile Gly Asn Asp Val Glu Asn Ala Ile Ala
                405                 410                 415
Thr Ala Val Gly Asp Asn Phe Val Trp Ala Tyr Gln Arg Ser Glu Ala
                420                 425                 430
Leu Ala Asp Asp Val Ala Arg Ser Phe Ala Asp Ala Gly Leu Asp Ser
        435                 440                 445
Val Leu Ser Ala Glu Leu Ser Pro His Val Met Gly Thr Asp Phe Gly
    450                 455                 460
Arg Leu Lys Ala Leu Gly Arg Met Glu Ser Lys Pro Leu Arg Arg Gly
465                 470                 475                 480
His Lys Met Ile Ile Gly Met Arg Gly Ser Tyr Gly Gly Val Val Met
                485                 490                 495
Ile Gly Met Leu Ser Ser Val Val Gly Leu Gly Leu Phe Asn Pro Leu
                500                 505                 510
Ser Val Gly Ala Gly Leu Ile Leu Gly Arg Met Ala Tyr Lys Glu Asp
        515                 520                 525
```

```
Lys Gln Asn Arg Leu Leu Arg Val Arg Ser Glu Ala Lys Ala Asn Val
    530                 535                 540

Arg Arg Phe Val Asp Asp Ile Ser Phe Val Val Ser Lys Gln Ser Arg
545                 550                 555                 560

Asp Arg Leu Lys Met Ile Gln Arg Leu Leu Arg Asp His Tyr Arg Glu
                565                 570                 575

Ile Ala Glu Glu Ile Thr Arg Ser Leu Thr Glu Ser Leu Gln Ala Thr
            580                 585                 590

Ile Ala Ala Gln Val Ala Glu Thr Glu Arg Asp Asn Arg Ile Arg
        595                 600                 605

Glu Leu Gln Arg Gln Leu Gly Ile Leu Ser Gln Val Asn Asp Asn Leu
    610                 615                 620

Ala Gly Leu Glu Pro Thr Leu Thr Pro Arg Ala Ser Leu Gly Arg Ala
625                 630                 635                 640

<210> SEQ ID NO 5
<211> LENGTH: 493
<212> TYPE: PRT
<213> ORGANISM: Mycobacterium tuberculosis

<400> SEQUENCE: 5

Met Ser Thr Ser Asp Arg Val Arg Ala Ile Leu His Ala Thr Ile Gln
1               5                   10                  15

Ala Tyr Arg Gly Ala Pro Ala Tyr Arg Gln Arg Gly Asp Val Phe Cys
            20                  25                  30

Gln Leu Asp Arg Ile Gly Ala Arg Leu Ala Glu Pro Leu Arg Ile Ala
        35                  40                  45

Leu Ala Gly Thr Leu Lys Ala Gly Lys Ser Thr Leu Val Asn Ala Leu
    50                  55                  60

Val Gly Asp Asp Ile Ala Pro Thr Asp Ala Thr Glu Ala Thr Arg Ile
65                  70                  75                  80

Val Thr Trp Phe Arg His Gly Pro Thr Pro Arg Val Thr Ala Asn His
                85                  90                  95

Arg Gly Gly Arg Arg Ala Asn Val Pro Ile Thr Arg Arg Gly Gly Leu
            100                 105                 110

Ser Phe Asp Leu Arg Arg Ile Asn Pro Ala Glu Leu Ile Asp Leu Glu
        115                 120                 125

Val Glu Trp Pro Ala Glu Glu Leu Ile Asp Ala Thr Ile Val Asp Thr
    130                 135                 140

Pro Gly Thr Ser Ser Leu Ala Cys Asp Ala Ser Glu Arg Thr Leu Arg
145                 150                 155                 160

Leu Leu Val Pro Ala Asp Gly Val Pro Arg Val Asp Ala Val Phe
                165                 170                 175

Leu Leu Arg Thr Leu Asn Ala Ala Asp Val Ala Leu Leu Lys Gln Ile
            180                 185                 190

Gly Gly Leu Val Gly Gly Ser Val Gly Ala Leu Gly Ile Ile Gly Val
        195                 200                 205

Ala Ser Arg Ala Asp Glu Ile Gly Ala Gly Arg Ile Asp Ala Met Leu
    210                 215                 220

Ser Ala Asn Asp Val Ala Lys Arg Phe Thr Arg Glu Leu Asn Gln Met
225                 230                 235                 240

Gly Ile Cys Gln Ala Val Val Pro Val Ser Gly Leu Leu Ala Leu Thr
                245                 250                 255

Ala Arg Thr Leu Arg Gln Thr Glu Phe Ile Ala Leu Arg Lys Leu Ala
            260                 265                 270
```

```
Gly Ala Glu Arg Thr Glu Leu Asn Arg Ala Leu Leu Ser Val Asp Arg
            275                 280                 285

Phe Val Arg Arg Asp Ser Pro Leu Pro Val Asp Ala Gly Ile Arg Ala
            290                 295                 300

Gln Leu Leu Glu Arg Phe Gly Met Phe Gly Ile Arg Met Ser Ile Ala
305                 310                 315                 320

Val Leu Ala Ala Gly Val Thr Asp Ser Thr Gly Leu Ala Ala Glu Leu
            325                 330                 335

Leu Glu Arg Ser Gly Leu Val Ala Leu Arg Asn Val Ile Asp Gln Gln
            340                 345                 350

Phe Ala Gln Arg Ser Asp Met Leu Lys Ala His Thr Ala Leu Val Ser
            355                 360                 365

Leu Arg Arg Phe Val Gln Thr His Pro Val Pro Ala Thr Pro Tyr Val
            370                 375                 380

Ile Ala Asp Ile Asp Pro Leu Leu Ala Asp Thr His Ala Phe Glu Glu
385                 390                 395                 400

Leu Arg Met Leu Ser Leu Leu Pro Ser Arg Ala Thr Thr Leu Asn Asp
            405                 410                 415

Asp Glu Ile Ala Ser Leu Arg Arg Ile Ile Gly Gly Ser Gly Thr Ser
            420                 425                 430

Ala Ala Ala Arg Leu Gly Leu Asp Pro Ala Asn Ser Arg Glu Ala Pro
            435                 440                 445

Arg Ala Ala Leu Ala Ala Ala Gln His Trp Arg Arg Ala Ala His
            450                 455                 460

Pro Leu Asn Asp Pro Phe Thr Thr Arg Ala Cys Arg Ala Ala Val Arg
465                 470                 475                 480

Ser Ala Glu Ala Met Val Ala Glu Phe Ser Ala Arg Arg
            485                 490

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Uniamp
      primer sequence

<400> SEQUENCE: 6
cctctgaagg ttccagaatc gatag                                         25

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Uniamp XhoI
      adapter sequence top strand

<400> SEQUENCE: 7
cctctgaagg ttccagaatc gatagctcga gt                                 32

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Uniamp XhoI
      adapter sequence bottom strand

<400> SEQUENCE: 8
```

```
actcgagcta tcgattctgg aaccttcaga ggttt                                35
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 9

```
gcgctggcgg gagatcgtca atg                                             23
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 10

```
tgcgcagtcg ggtcacagga gtcg                                            24
```

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 11

```
tcccgccgcc gaacaccta                                                  19
```

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 12

```
ggatccggcc gaccagaga                                                  19
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 13

```
ggagtacggc cgcaaggcta aaac                                            24
```

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 14

```
cagaccccga tccgaactga gacc                                            24
```